(12) United States Patent
Chakrabarti et al.

(10) Patent No.: US 7,829,677 B2
(45) Date of Patent: Nov. 9, 2010

(54) ANTIBODIES THAT RECOGNIZE HYPERPROLIFERATIVE CELLS AND METHODS OF MAKING AND USING SAME

(75) Inventors: Subhra Chakrabarti, Banjara Hills (IN); Sonjoy Mukerjee, San Diego, CA (US); Mark C. Glassy, San Diego, CA (US)

(73) Assignee: Shantha West, Inc., San Diego, CA (US)

( * ) Notice: Subject to any disclaimer, the term of this patent is extended or adjusted under 35 U.S.C. 154(b) by 0 days.

(21) Appl. No.: 12/238,309

(22) Filed: Sep. 25, 2008

(65) Prior Publication Data
US 2009/0087442 A1    Apr. 2, 2009

Related U.S. Application Data

(62) Division of application No. 11/567,686, filed on Dec. 6, 2006, now Pat. No. 7,446,178, which is a division of application No. 10/662,044, filed on Sep. 11, 2003, now Pat. No. 7,238,353.

(60) Provisional application No. 60/410,366, filed on Sep. 11, 2002.

(51) Int. Cl.
C07K 16/00    (2006.01)
(52) U.S. Cl. .................. 530/388.1; 424/178.1
(58) Field of Classification Search ............. 530/388.1; 424/178.1
See application file for complete search history.

(56) References Cited

U.S. PATENT DOCUMENTS

| 5,286,647 | A  | 2/1994 | Handley et al. |
|---|---|---|---|
| 2002/0098581 | A1 | 7/2002 | Glassy et al. |

FOREIGN PATENT DOCUMENTS

| WO | WO-97-39774 A | 10/1997 |
|---|---|---|
| WO | WO-99-43815 A | 9/1999 |

OTHER PUBLICATIONS

Stanton, P et al, 1994, Br J Cancer, 70: 427-433.*
Iehle, C et al, 1999, J Steroid Biochem Mol Biol, 68: 189-195.*
Geng et al, Cellular and molecular immunology (China), 2006, 3 (6), p. 439-43.*
Rudikoff et al, PNAS, USA, 1982, 79: 1979.*
Glassy, M.C. et al., "Requirements for human antibody cocktails for oncology," Exp. Op. Biol. Ther. 5(10):1333-1338 (2005).
Mukerjee, S. et al., "Co-expression of tumor antigens and their modulation by pleiotrophic modifiers enhance targeting of human monoclonal antibodies to pancreatic carcinoma," Human Antibodies 9:9-22 (1999).
Mukerjee, S. et al., "Characterization of human IgG1 monoclonal antibody against gangliosides expressed on tumor cells," Hybridoma 17(2):133-142 (1998).
Yano, Y. et al., "Immunohistological Characterization of Human Monoclonal Antibody Against Lung Cancer," J. Surgical Oncol. 39:108-113 (1988).
Buskens, C. et al., "Adenocarcinomas of the Gastro-Esophageal Junction: A Comparative Study of the Gastric Cardia and the Esophagus with Respect to Cyclooxygenase-2 Expression," Digestive Disease Week Abstracts and Itinerary Planner, vol. 2003, abstract No. 850, 2003, e-file.
Gura, T., "Systems for Identifiyng New Drugs Are Often Faulty," Science vol. 278:1041-1042, Nov. 7, 1997.
Karaczyn, A. et al., "The Octapeptidic End of the C-Terminal Tail of Histone H2A Is Cleaved Off in Cells Exposed to Carcinogenic Nickel (II)," Chem. Res. Toxicol. 16:1555-1559 (2003).
Martin, A. and Weber, B.L., "Genetic and Hormonal Risk Factors in Breast Cancer," J. of the National Cancer Inst., vol. 92, No. 14, Jul. 19, 2000.
Mylonas, M. et al., "An extremely stable Ni(II) complex derived from the hydrolytic cleavage of the C-terminal tail of histone H2A," J. Inorg. Biochem. 99:637-643 (2005).
White, C.A., et al., "Antibody-Targeted Immunotherapy for Treatment of Malignancy," Annu. Rev. Med. 2001, 52:125-45.
Oct. 2005, "Temporary protocol of treatment: Trastuzumab (Herceptin®) in adjuvant conditions," Institu National de Cancer and Agence francaise de securite sanitaire des produits de sante, www.e-cancer.fr/medias/pttdefeng2710.pdf, Web site. Ref cannot be published.
Bowie, J.U. et al., "Deciphering the Message in Protein Sequences: Tolerance in Amino Acid Substitutions," Science 257:1306-1310 (1990).
Burgess, W.H. et al., "Activities of Heparin-binding (Acidic Fibroblast) Growth Factor-1 from Its Receptor-Binding Activities by Site-directed Mutagenesis of a Single Lysine Residue," J. Cell. Biol. 111:2129-2138 (1990).
Gillies, S.D. and Wesolowski, J.S., "Antigen binding and biological activities of engineered mutant chimeric antibodies with human tumor specificities," Human Antibodies and Hybridomas 1(1):47-54 (1990).
Paul, W.E., 3$^{rd}$ ed. 1993, Fundamental Immunology, p. 242.
Tao, M.H. and Morrison, S.L., "Studies of Agylcosylated Chimeric Mouse-Human IgG: Role of Carbohydrate in the Structure and Effector Functions Mediated by the Human IgG Constant Region," J. Immunol. 143(8):2595-2601 (1989).

* cited by examiner

*Primary Examiner*—Larry R. Helms
*Assistant Examiner*—Minh-Tam Davis
(74) *Attorney, Agent, or Firm*—Wilson Sonsini Goodrich & Rosati

(57) ABSTRACT

The invention relates to antibodies that bind to antigens, such as antigens associated with hyperproliferating cells, and methods of treating hyperproliferative disorders. The invention antibodies are useful for treating hyperproliferative disorders, such as neoplasia.

19 Claims, 3 Drawing Sheets

ANTIBODIES THAT RECOGNIZE HYPERPROLIFERATIVE CELLS AND METHODS OF MAKING AND USING SAME

CROSS-REFERENCE

This application is a divisional application of U.S. patent application Ser. No. 11/567,686, filed Dec. 6, 2006, which is issued as U.S. Pat. No. 7,446,178, which is a divisional application of U.S. patent application Ser. No. 10/662,044, filed Sep. 11, 2003, which issued as U.S. Pat. No. 7,238,353 on Jul. 3, 2007, which is incorporated herein by reference in its entirety, and which claims the benefit of priority application Ser. No. 60/410,366, filed on Sep. 11, 2002, which is also incorporated herein by reference in its entirety and to which application we claim priority under 35 U.S.C. §120.

FIELD OF THE INVENTION

The invention relates to antibodies that bind to antigens associated with hyperproliferating cells, and methods of treating hyperproliferative disorders.

BACKGROUND

Classical antineoplastic therapeutic strategies such as surgery, radiation, and chemotherapy not only fail to cure the great majority of neoplasms, but their employment often leads to severe and debilitating side effects. The potential of antibodies as "magic bullets" for cancer therapy has been appreciated for nearly a century. During the past 25 years, various scientific developments have made possible the production of unlimited quantities of clinical-grade murine, chimeric, and humanized monoclonal antibodies (MoAbs).

Immunotherapy as a fourth anti-cancer therapy has already been proven to be quite effective. Intact, unconjugated MoAbs may: [1] produce anticancer effects through the immune system on the basis of interactions between the Fc portion of antibody and complement proteins and/or effector cells; [2] induce regulatory effects by neutralizing circulating ligands or blocking cell membrane receptors, thereby interfering with ligand/receptor interactions and signal transduction; [3] serve as immunogens for anti-cancer vaccines through the anti-idiotype-network cascade. Conjugated MoAbs can serve as carriers of other agents such as radioisotopes, natural toxins, chemotherapy drugs, cytokines, and immune cells. Important aspects of the antigenic target are the degree to which it is tumor-specific or tumor-associated, whether it internalizes or not, whether it is shed, the density of expression, and the physiologic significance of the antigen to the target cell.

In the 1980s investigators established the safety of antibody administration, defined certain predictable antibody-mediated toxicities, and confirmed that antibodies could reach tumor targets and produce antitumor effects. However, clinical use of nonhuman antibodies in humans is limited due to the development of an anti-globulin immune response in the host. This limitation has been overcome with the production of antibodies with varying degrees of humanization. For example, engineered chimeric human-mouse MoABs have been developed by replacing the mouse Fc region with the human constant region. Moreover, the framework regions of variable domains of rodent immunoglobulins were also replaced by their human equivalents. In 1997 rituximab (Rituxan), a mouse-human chimeric anti-CD20, became the first MoAb approved by regulatory agencies for the treatment of a human malignancy.

SUMMARY

Isolated human polyclonal and monoclonal antibodies are provided. In one embodiment, an antibody is designated RM4 (ATCC deposit No. PTA-5412) and selectively binds to an antigen designated AgRM4. In another embodiment, an antibody is designated RM2 (ATCC deposit No. PTA-5411) and selectively binds to an antigen designated AgRM2.

Antibodies having significant binding affinity for AgRM4 and AgRM2; having the binding specificity of the antibody of RM4 and RM2; that compete for the binding of the RM4 or RM2 antibody of AgRM4 and AgRM2, respectively; and that bind to an epitope of AgRM4 or AgRM4 and AgRM2 to which the antibody RM4 or RM2 binds, are provided. Exemplary antibodies having the binding specificity of RM4 and RM2 have a binding affinity for AgRM4 and AgRM2, respectively, within 1000-fold, within 100-fold, and within 10-fold of RM4 and RM2 antibodies.

Modified antibodies, such as substitutions, additions and deletions of RM4 and RM2 are provided. Exemplary modified antibodies deviate from the light chain or the heavy chain amino acid sequence of RM4 (ATCC deposit No. PTA-5412) and RM2 (ATCC deposit No. PTA-5411), provided that the modified antibody binds to AgRM4 and AgRM2, respectively. Exemplary deletions include Fab, Fab', Fv, F(ab')$_2$, Fd, and single chain Fv.

Modified antibodies that include attached or incorporated molecular entities are further provided. Such entities include cytotoxic molecules (e.g., bacterial toxin, plant toxin, alpha, beta or gamma radionuclide, cytotoxic drug, or cytokine), detectable labels and tags (e.g., radioisotopes, fluorescent compound, colloidal metal, chemiluminescent compound, bioluminescent compound, enzyme and paramagnetic labels).

Because AgRM2 and AgRM4 have been found to be expressed in proliferating cells, for example, in part on the cell surface, the invention includes antibodies that bind to hyperproliferating cells in any cell, tissue or organ type (e.g., breast, colon, gut, or lung cell). Exemplary hyperproliferating cells include metastatic and non-metastatic cancer or neoplastic cells (e.g., of the breast, colon, gut, or lung).

Further provided are nucleic acids that encode RM4 (ATCC deposit No. PTA-5412) and RM2 (ATCC deposit No. PTA-5411), both full length and subsequences thereof, cells that contain the nucleic acids (e.g., transformed cells and hybridoma cells) and cells that express invention antibodies.

Antibody combination compositions are also provided. In one embodiment, a composition includes an RM4 (ATCC deposit No. PTA-5412) or an RM2 (ATCC deposit No. PTA-5411) antibody, and one or more anti-tumor or immune enhancing agents (e.g., an antibody that binds to an antigen). In another embodiment, a composition includes an RM4 (ATCC deposit No. PTA-5412) and RM2 (ATCC deposit No. PTA-5411) antibody.

Kits including compositions of the invention are additionally provided (e.g., combination compositions, pharmaceutical compositions). Kits can include instructions for use in a method of the invention, in vitro, ex vivo or in vivo.

Pharmaceutical compositions including antibodies of the invention (e.g., RM4 or RM2), and a pharmaceutically acceptable carrier, are also provided.

Methods of producing antibodies of the invention are provided. In one embodiment, a nucleic acid that encodes an invention antibody is introduced into a host cell or a translation extract, and the host cell or extract is incubated under conditions whereby the nucleic acid is expressed as a translation product, and the antibody isolated.

Also provided are methods of detecting AgRM4 and AgRM2, in a sample in vitro and in vivo (e.g., in a subject or biological sample from a subject). In one embodiment, a method includes contacting AgRM4 or a sample that may contain AgRM4 with RM4 under conditions allowing the antibody to bind AgRM4; and assaying for the presence of AgRM4. In another embodiment, a method includes contacting AgRM2 or a sample that may contain AgRM2 with RM2 under conditions allowing the antibody to bind AgRM2; and assaying for the presence of AgRM2.

Methods of identifying inhibitors and stimulators of AgRM4 and AgRM2 expression are provided. In one embodiment, a method includes contacting a cell that expresses or is capable of expressing AgRM4 with a test compound; and detecting expression of said AgRM4. In another embodiment, a method includes contacting a cell that expresses or is capable of expressing AgRM2 with a test compound; and detecting expression of said AgRM2. A change in AgRM4 or AgRM2 expression indicates that the test compound is an inhibitor or stimulator of AgRM4 or AgRM2 expression.

Methods of inhibiting or preventing the proliferation of a cell (e.g., a proliferating or hyperproliferating cell) in vitro, ex vivo and in vivo (e.g., in a mammalian subject such as a human) that expresses AgRM4 or AgRM2 are provided. In one embodiment, a method includes contacting the cell with an amount of antibody (e.g., RM4 or RM2) sufficient to inhibit or prevent proliferation of the cell. Exemplary cells include brain, skin, breast, colon, gut, lung, and pancreatic cells. Exemplary hyperproliferating cells include metastatic and non-metastatic cancer cells.

Methods of treating hyperproliferative cell disorders, including tumors, cancers and neoplasia, are provided. In one embodiment, a method includes administering to a subject an amount of antibody sufficient to treat the hyperproliferative cell disorder. In another embodiment, a method includes administering to a subject an amount of human monoclonal antibody designated RM4 (ATCC deposit No. PTA-5412) effective to treat the subject. In yet another embodiment, a method includes administering to a subject an amount of human monoclonal antibody designated RM2 (ATCC deposit No. PTA-5411) effective to treat the subject. In still another embodiment, a method includes administering to a subject an amount of human monoclonal antibody designated RM4 (ATCC deposit No. PTA-5412) or RM2 (ATCC deposit No. PTA-5411) and an immune enhancing or anti-tumor agent effective to treat the subject. In still a further embodiment, a method includes administering to a subject an amount of human monoclonal antibody designated RM4 (ATCC deposit No. PTA-5412) and designated RM2 (ATCC deposit No. PTA-5411) effective to treat the subject.

Tumors treated in accordance with the invention include stage I, II, III, IV and V tumors; metastatic and non-metastatic tumors; solid and liquid tumors; tumors located at least in part in brain, skin, breast, colon, gut, lung, and pancreas; hematopoetic tumors; sarcomas, carcinomas, melanomas, myelomas, blastomas, lymphomas and leukemias. Candidate treatment subjects include subjects undergoing, or having undergone anti-cell proliferative (e.g., anti-tumor) therapy.

Treatments include reducing one or more adverse symptoms associated with the tumor. Treatments also include reducing tumor volume, inhibiting an increase in tumor volume, inhibiting a progression or worsening of the tumor, stimulating tumor cell lysis or apoptosis, and reducing or inhibiting tumor metastasis. Treatments further include reducing mortality of the subject.

Methods of screening for the presence of a hyperproliferative disorders are provided. In one embodiment, a method includes contacting a tissue in vitro or in vivo with an RM4 antibody (ATCC deposit No. PTA-5412) or an RM2 antibody (ATCC deposit No. PTA-5411), and assaying for the presence of AgRM4 or AgRM2. The presence of AgRM4 or AgRM2 in the tissue indicates the presence of a hyperproliferative disorder.

DETAILED DESCRIPTION

Figure 1:
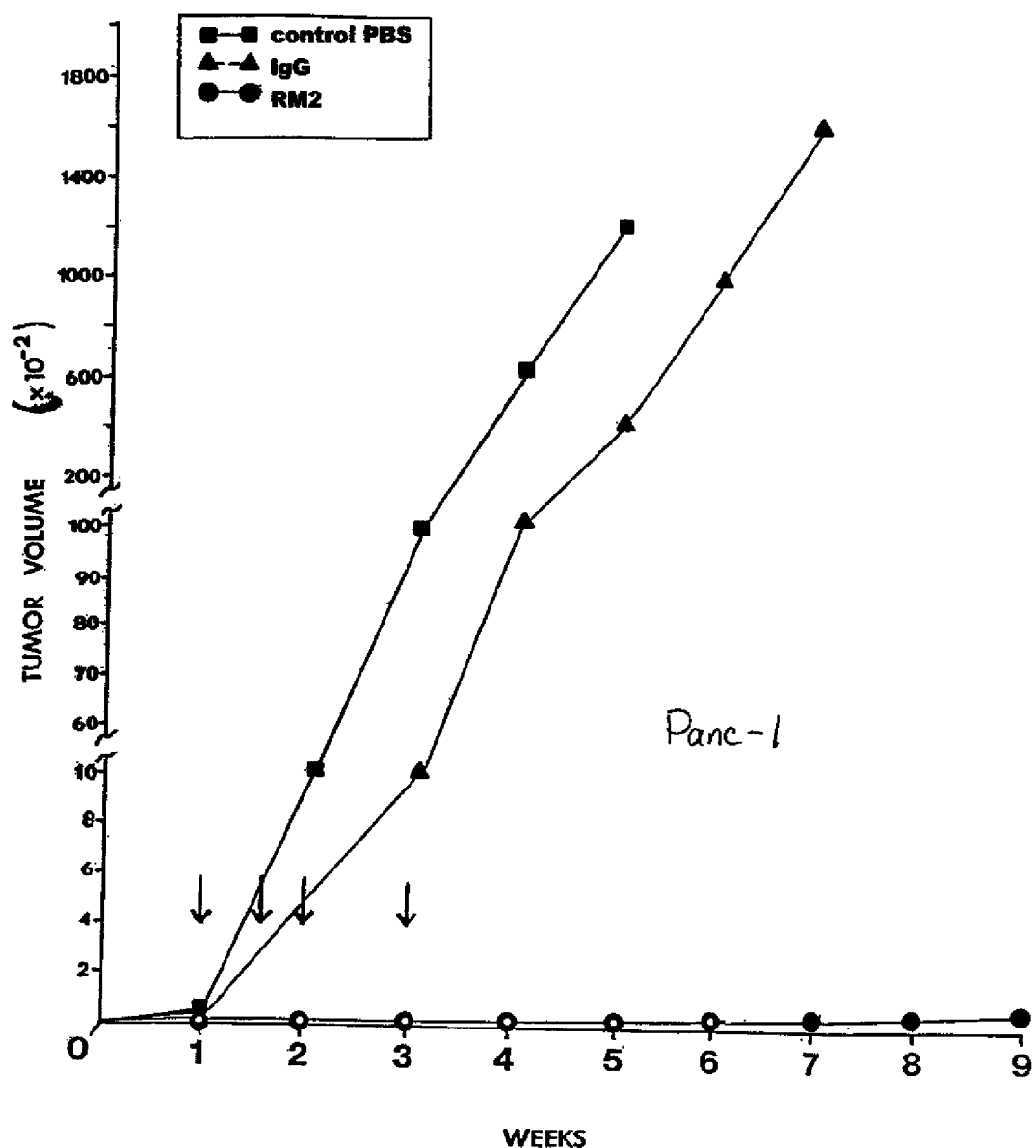
FIG. 1 shows tumor (Panc-1 cells, a pancreatic cancer cell line) necrosis in mice following injection with RM2. Tumor volume for each week following injection is illustrated.

The invention is based, at least in part, on the isolation and characterization of human antibodies that selectively bind to hyperproliferative cells, including tumor cells in vivo. That is, the antibodies preferentially bind to hyperproliferating cells in comparison to non-proliferating cells. Thus, the antibodies are useful for detecting and screening for the presence of hyperproliferative cells and the antigens to which the antibodies bind. In addition, the antibodies are cytotoxic towards hyperproliferating cells to which they bind when administered in a sufficient amount. For example, as exemplified herein, an invention antibody, for example, RM4 (ATCC deposit No. PTA-5412), is able to induce tumor regression (reduce tumor volume) in mice bearing tumors (see, for example, FIGS. 2 and 3). Thus, antibodies of the invention are useful for treating undesirable, excessive or abnormal cell proliferation including for example, non-metastatic and metastatic tumors.

In accordance with invention, isolated antibodies, methods of making the antibodies and methods of using the antibodies, including therapeutic and diagnostic methods, are provided. The invention antibodies are capable of selectively binding to antigens associated with hyperproliferating cells. In one embodiment, an invention antibody is an isolated human monoclonal antibody designated RM4 that selectively binds to an antigen designated AgRM4.

Exemplary antibody RM4 is produced by a human IgG secreting cell line derived using standard somatic cell hybridization technology (ATCC deposit No. PTA-5412). ATCC Deposit No. PTA-5412 for hybridoma RM4 was deposited with the American Type Culture Collection (ATCC) on Aug. 22, 2003; American Type Culture Collection, 10801 University Blvd., Manassas, Va. 20110-2209. The antibody secreting B cell was obtained from pooled regional draining lymph nodes of cancer patients and immortalized with RN15, a WIL-2 derived human fusion partner. RM4 recognizes a cell surface (extracellular matrix) component (AgRM4). AgRM4 is expressed at least in part on the cell surface. AgRM4 is more highly expressed in proliferating cells than in non-proliferating cells, e.g., hyperproliferating cells. AgRM4 is present on metastatic or non-metastatic breast, colon, gut and lung cancer cells.

As used herein, the term "antibody" refers to a protein that binds to other molecules (antigens) via heavy and light chain variable domains, $V_H$ and $V_L$, respectively. Antibodies include IgG, IgD, IgA, IgM and IgE, subtypes, and mixtures thereof. The antibodies may be polyclonal or monoclonal, intact immunoglobulin molecules, two full length heavy chains linked by disulfide bonds to two full length light chains, or subsequences (i.e. fragments) thereof, with our without constant region, that bind to an epitope of an antigen, and mixtures thereof. Antibodies may comprise heavy or light chain variable regions, $V_H$ or $V_L$, individually, or in any combination.

The terms "protein," "polypeptide" and "peptide" are used interchangeably herein to refer to two or more covalently linked amino acids, or "residues," through an amide bond or equivalent Polypeptides are of unlimited length and the amino acids may be linked by non-natural and non-amide chemical bonds including, for example, those formed with glutaraldehyde, N-hydroxysuccinimide esters, bifunctional maleimides, or N,N'-dicyclohexylcarbodiimide (DCC). Non-amide bonds include, for example, ketomethylene, aminomethylene, olefin, ether, thioether and the like (see, e.g., Spatola (1983) in Chemistry and Biochemistry of Amino Acids, Peptides and Proteins, Vol. 7, pp 267-357, "Peptide and Backbone Modifications," Marcel Decker, N.Y.).

As used herein, the term "isolated," when used as a modifier of an invention composition (e.g., antibodies, modified forms, subsequences, nucleic acids encoding same, cells, vectors, etc.), means that the compositions are made by the hand of man or are separated from their naturally occurring in vivo environment. Generally, compositions so separated are substantially free of one or more materials with which they normally associate with in nature, for example, one or more protein, nucleic acid, lipid, carbohydrate, cell membrane. Thus, an isolated antibody is typically substantially free of one or more materials with which it may typically associate with in nature. The term "isolated" does not exclude alternative physical forms, such as polypeptide multimers, post-translational modifications (e.g., phosphorylation, glycosylation) or derivatized forms.

An "isolated" antibody can also be "substantially pure" when free of most or all of the materials with which it typically associates with in nature. Thus, an isolated molecule that also is substantially pure does not include polypeptides or polynucleotides present among millions of other sequences, such as antibodies of an antibody library or nucleic acids in a genomic or cDNA library, for example. Of course, a "substantially pure" molecule can be combined with one or more other molecules. Thus, the term "substantially pure" does not exclude combination compositions.

Substantial purity can be at least about 60% or more of the molecule by mass. Purity can also be about 70% or 80% or more, and can be greater, for example, 90% or more. Purity can be determined by any appropriate method, including, for example, UV spectroscopy, chromatography (e.g., HPLC, gas phase), gel electrophoresis (e.g., silver or coomassie staining) and sequence analysis (nucleic acid and peptide).

The invention further provides antibodies having the binding specificity of the antibodies set forth herein. In one embodiment, the antibody has the binding specificity of RM4. In one aspect, the binding is specific for AgRM4.

The invention additionally provides antibodies that compete with the binding of the antibodies set forth herein, and antibodies that bind to an epitope of AgRM4 to which an antibody of the invention binds. In one embodiment, the antibody competes with the binding of RM4 to an antigen. In another embodiment, the antibody binds to an epitope of AgRM4 to which an antibody of the invention binds. In one aspect, the antibody competes with the binding of RM4 to AgRM4.

As used herein, the term "bind" or "binding" means that the compositions referred to have affinity for each other. The term "specific" or "selective," and grammatical variations thereof when used in reference to binding, means that the binding between the molecules is such that it can be distinguished from non-specific or non-selective binding to other molecules using an assay such as ELISA, immunoprecipitation, coprecipitation, western blotting, two-hybrid assays and the like. Appropriate controls can be used to distinguish between "specific" and "non-specific" binding. For example, specific or selective binding typically has a dissociation constant ($K_D$) of less than about $1 \times 10^{-5}$ M or less than about $1 \times 10^{-6}$ M, $1 \times 10^{-7}$ M, $1 \times 10^{-8}$ M, $1 \times 10^{-9}$ M, or $1 \times 10^{-10}$ M. In contrast, non-specific binding typically has significantly less affinity, for example, a $K_D$ greater than $10^{-3}$ M. Thus, selective binding can be distinguished from non-selective binding by measuring dissociation constant of the complex. Selective binding can also be distinguished form non-selective binding by increasing the stringency of the binding assay. A particular example of specific binding is that which occurs between an antibody and an antigen.

As used herein, the term "epitope" means an antigenic determinant to which an antibody binds. A polypeptide epitope can be as few as three amino acids, yet generally an epitope has at least five amino acids or more, e.g., at least eight to 12 amino acids. A "conformational epitope" is an epitope comprised of a two or three dimensional juxtaposition of amino acids; the amino acids can be contiguous or non-contiguous on the same polypeptide or on one or more different polypeptides.

Antibodies having substantially the same (e.g., within about 10-fold) and having different binding affinity from the antibodies set forth herein are also provided. In one embodiment, an antibody has increased or decreased affinity for the antigen (e.g., AgRM4) in comparison to a reference antibody (e.g., RM4). In one aspect, an antibody has a binding affinity for AgRM4 within 1000-fold of the RM4 antibody. In additional aspects, the antibodies having different binding affinity from the antibodies set forth herein are within 2-5, 5-10, 10-50, 50-100, 100-1000 and 1000-10,000 fold of RM4 antibody heavy and light chain sequences.

Antibodies having significant binding affinity for AgRM4 are also provided. As used herein, the term "significant" or "substantial" when used in reference to binding affinity or activity, means that the dissociation constant ($K_D$) of the complex (e.g., antibody-antigen complex) is not less than $10^{-3}$ M. In other words, for significant binding affinity or activity, the $K_D$ must be less than $10^{-3}$ M, e.g., $10^{-4}$ M, $10^{-5}$ M, $10^{-6}$ M, $10^{-7}$ M, $10^{-8}$ M, etc. Typically, the $K_D$ of an antibody-antigen complex is about $10^{-5}$ M to about $10^{-6}$ M or less.

Antibodies of the invention include modified forms of the antibodies set forth herein, provided that the modified antibody retains, at least a part of, a function or activity of the unmodified or reference antibody. For example, a modified RM4 antibody may retain antigen binding specificity, e.g., bind an epitope present in AgRM4, but have increased or decreased binding affinity for AgRM4 relative to unmodified RM4.

Thus, invention antibodies further include antibodies having sequences distinct from the RM4 antibody heavy and light chain sequences. In various embodiments, an antibody has the binding specificity of RM4, competes for RM4 binding to AgRM4, and binds to an epitope of AgRM4 to which an antibody of the invention binds.

The term "modify" and grammatical variations thereof, when used in reference to a composition such as a polypeptide or nucleic acid, means that the modified composition deviates from a reference composition. Polypeptide modifications include amino acid substitutions, additions and deletions, which are also referred to as "variants." Polypeptide modifications also include one or more D-amino acids substituted for L-amino acids (and mixtures thereof), structural and functional analogues, for example, peptidomimetics having synthetic or non-natural amino acids or amino acid analogues and derivatized forms. Polypeptide modifications further include fusion (chimeric) polypeptide sequences, which is an amino acid sequence having one or more molecules not normally present in a reference native (wild type) sequence covalently attached to the sequence, for example, one or more amino acids. Modifications include cyclic structures such as an end-to-end amide bond between the amino and carboxy-terminus of the molecule or intra- or inter-molecular disulfide bond. Polypeptides including antibodies may be modified in vitro or in vivo, e.g., post-translationally modified to include, for example, sugar residues, phosphate groups, ubiquitin, fatty acids or lipids.

Thus, the invention provides antibodies having one or more modifications, provided that the modified antibody retains an activity or function of a reference antibody (e.g., antigen binding activity). In one embodiment, the antibody is modified from a light chain or the heavy chain amino acid sequence of RM4. In one aspect, a modified antibody has an amino acid substitution, addition or deletion (e.g., 1-3, 3-5, 5-10 or more) of the variable or constant region, heavy or light chain. In another aspect, the modified antibody comprises a subsequence (e.g., Fab, Fab', Fv, F(ab')$_2$, Fd, or single chain Fv). In yet another aspect, the substitution is with a human or non-human amino acid which is structurally similar to the human residue. In a particular aspect, the substitution is a conservative amino acid substitution.

A "conservative substitution" means the replacement of one amino acid by a biologically, chemically or structurally similar residue. Biologically similar means that the substitution is compatible with biological activity, e.g., antigen binding. Structurally similar means that the amino acids have side chains with similar length, such as alanine, glycine and serine, or having similar size. Structurally similar substitutions are unlikely to alter antigenicity of the antibody relative to the unsubstituted antibody. Chemical similarity means that the residues have the same charge or are both hydrophilic or hydrophobic. Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like.

Invention antibodies having a sequence not identical to a sequence of heavy and light chain amino acid sequences of RM4 include antibodies having an amino acid sequence with 50%, 60%, 70%, 75%, 80%, 85%, 90%, 95%, 96%, 97%, 98%, or more identity to a heavy or light chain amino acid sequence of RM4. The identity can be over a defined area of the antibody, e.g., one or more complementarity determining regions (CDRs) or framework region. The term "identical" or "identity" means that two or more referenced entities are the same. Thus, where two protein sequences are identical, they have the same amino acid sequence. "Areas of identity" means that a portion of two or more referenced entities are the same. Thus, where two protein sequences are identical over one or more sequence regions they share amino acid identity in these regions. The term "substantial identity" means that the identity is structurally or functionally significant. That is, the identity is such that the molecules are structurally identical or have at least one of the same functions (e.g., biological function) even though the molecules differ.

Due to variation in the amount of sequence conservation between structurally and functionally related proteins, the amount of sequence identity for substantial identity will depend upon the type of protein, the region and its function. For proteins there can be as little as 30% sequence identity, but typically there is more, e.g., 50%, 60%, 75%, 85%, 90%, 95%, 96%, 97%, 98%, identity to a reference sequence. For nucleic acid sequences, 50% sequence identity or more typically constitutes substantial homology, but can vary depending on the comparison region.

The extent of identity between two sequences can be ascertained using a computer program and mathematical algorithm known in the art. Such algorithms that calculate percent sequence identity (homology) generally account for sequence gaps and mismatches over the comparison region. For example, a BLAST (e.g., BLAST 2.0) search algorithm (see, e.g., Altschul et al. (1990) J. Mol. Biol. 215:403-10, publicly available through NCBI) has exemplary search parameters as follows: Mismatch-2; gap open 5; gap extension 2. For polypeptide sequence comparisons, a BLASTP algorithm is typically used in combination with a scoring matrix, such as PAM100, PAM 250, and BLOSUM 62.

As used herein, the term "subsequence" or "fragment" means a portion of the full length molecule. For example, a subsequence of an antibody is at least one amino acid less in length than full length antibody having intact heavy and light chain sequence (e.g. one or more internal or terminal amino acid deletions from either amino or carboxy-termini). Subsequences therefore can be any length up to the full length molecule.

Subsequences include portions which retain at least part of the function or activity of a full length antibody or a reference antibody sequence. For example, an antibody subsequence will retain the ability to selectively bind to an antigen (e.g., AgRM4) even though the binding affinity of the subsequence may be greater or less than the binding affinity of the full length reference antibody. Subsequences can comprise a portion of any of the invention antibody sequences, for example, a portion of $V_H$ or $V_L$ domain of RM4. Specific examples of antibody subsequences of the invention include, for example, Fab, Fab', Fv, F(ab')$_2$, Fd, or single chain antibody (SCA) fragment (e.g., scFv). Additional fragments are known in the art and described, for example, in Hudson, Curr. Opin. Biotechnol. 9:395 (1998).

Pepsin or papain digestion of whole antibodies can be used to generate subsequences. For example, Fab can be produced by digestion of a whole antibody with the enzyme papain, to yield a fragment consisting of an intact light chain and a portion of a heavy chain. (Fab')$_2$ can be produced by treating a whole antibody with the enzyme pepsin, without subsequent reduction. An Fab' antibody fragment can be produced from (Fab')$_2$ by reduction with a thiol reducing agent, which yields a molecule consisting of an intact light chain and a portion of a heavy chain. Two Fab' fragments are produced per antibody molecule treated in this manner.

An Fv fragment is a fragment containing the variable region of a light chain $V_L$ and the variable region of a heavy chain $V_H$ expressed as two chains. The association may be non-covalent or may be covalent, such as a chemical cross-linking agent or an intermolecular disulfide bond (Inbar et al., (1972) Proc. Natl. Acad. Sci. USA 69:2659; Sandhu (1992) Crit. Rev. Biotech. 12:437).

A single chain antibody (SCA) is a genetically engineered or enzymatically digested antibody containing the variable region of a light chain $V_L$ and the variable region of a heavy chain, optionally linked by a flexible linker, such as a polypeptide sequence, in either $V_L$-linker-$V_H$ orientation or in $V_H$-linker-$V_L$ orientation. Alternatively, a single chain Fv fragment can be produced by linking two variable domains via a disulfide linkage between two cysteine residues. Methods for producing scFv antibodies are described, for example, by Whitlow et al., (1991) In: Methods: A Companion to Methods in Enzymology 2:97; U.S. Pat. No. 4,946,778; and Pack et al., (1993) Bio/Technology 11:1271.

Other methods of producing antibody subsequences, such as separation of heavy chains to form monovalent light-heavy chain fragments, further cleavage of fragments, or other enzymatic, chemical, or genetic techniques may also be used, provided that the subsequences have a function or activity, e.g., bind to the antigen to which the intact antibody binds.

Modified forms also include derivatized sequences, for example, amino acids in which free amino groups form amine hydrochlorides, p-toluene sulfonyl groups, carbobenzoxy groups; the free carboxy groups from salts, methyl and ethyl esters; free hydroxl groups that form O-acyl or O-alkyl derivatives, as well as naturally occurring amino acid derivatives, for example, 4-hydroxyproline, for proline, 5-hydroxylysine for lysine, homoserine for serine, ornithine for lysine, etc. Modifications can be produced using any of a variety of methods well known in the art (e.g., PCR based sited-directed, deletion and insertion mutagenesis, chemical modification and mutagenesis, cross-linking, etc.).

Antibodies of the invention can be either joined directly or indirectly through covalent or non-covalent binding, e.g. via a multimerization domain, to produce multimers. Specific examples of domains that confer multimer formation include coiled-coil (e.g., leucine zipper structures) and alpha-helical protein sequences. Sequences that mediate protein-protein binding via Van der Waals' forces, hydrogen bonding or charge-charge bonds are also contemplated as multimerization domains. One specific example of a multimerization domain is p53 residues 319 to 360, which mediates tetramer formation. Another example is extracellular protein TSP4, a member of the thrombospondin family, which can form pentamers. Additional specific examples are the leucine zippers of jun, fos, and yeast protein GCN4.

The antibodies of the invention therefore also include multimers. A multimer can be a dimer, trimer, tetramer or other higher order oligomer. Multimers can be combinations of the same antibodies (homo-oligomers) or different antibodies (hetero-oligomers), the different antibodies being human, humanized or non-human.

Antibodies of the invention can be modified to include one or more functions or activities in addition to binding a particular antigen. For example, an antibody can include a region that binds to a different antigen, or have a function distinct from antigen binding. Such modified antibodies are referred to herein as "multifunctional antibodies," and include, for example, multispecific (e.g., bispecific, trispecific, tetraspecific, etc.) antibodies. The term "multispecific" refers to an antibody that binds to two or more different antigenic epitopes. The different epitopes may be present on the same antigen or different antigens. For example, a multispecific antibody oligomer comprises a mixture of two or more antibodies each having different epitope binding specificity and which form a multimer. The different epitopes may be expressed by the same or a different cell.

The term "multifunctional" means that the composition referred to has two or more activities or functions. Particular non-limiting examples include, for example, antigen binding, enzyme activity, ligand or receptor binding (substrates, agonists and antagonists), detection, purification, and toxicity.

The term "detectable label" refers to a molecule that can be conjugated to another molecule so as to enable detection of the conjugated molecule. Examples of detectable labels include chelators, photoactive agents, radionuclides (alpha, beta and gamma emitters), fluorescent agents and paramagnetic ions. Th term "tag" refers to a molecule conjugated to another that allows detection or purification. Specific examples of tags include immunoglobulins, T7, polyhistidine tags, glutathione-S-transferase, a chitin-binding tag, calmodulin-binding tag, myc tag, and a Xpress epitope (detectable by anti-Xpress antibody; Invitrogen, Carlsbad, Calif., USA).

An antibody that has an attached polypeptide with enzyme activity (e.g., green fluorescent protein, acetyltransferase, galactosidase, glucose oxidase, peroxidase, horseradish peroxidase (HRP), urease and alkaline phosphatase) is one particular example of a multifunctional antibody. Attached polypeptides also include apoptotic factors, differentiative factors, chemokines and cytokines (interleukins, interferons).

Additional candidate functions for multifunctional antibodies other than antigen binding include, for example, radioactive (e.g., $^3$H, $^{14}$C, $^{32}$P, $^{33}$P, $^{35}$S, $^{125}$I, $^{131}$I) and non-radioactive moieties (e.g., gold particles, colored glass or plastic polystyrene, polypropylene, or latex beads) and amino acid sequences (e.g., tags, as set forth herein) for detection.

Detectable moieties also include fluorescent compounds (e.g., fluorescein isothiocyanate, rhodamine, phycocrytherin, phycocyanin, allophycocyanin, o-phthaldehyde, fluorescamine, and commercially available fluorophores such as Alexa Fluor 350, Alexa Fluor 488, Alexa Fluor 532, Alexa Fluor 546, Alexa Fluor 568, Alexa Fluor 594, Alexa Fluor 647, and BODIPY dyes such as BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 60, rhodamine green, rhodamine red, tetramethylrhodamine and Texas Red, from Molecular Probes, Inc., Eugene, Oreg.), colloidal metals, chemiluminescent compounds (e.g., luminol, isoluminol, an aromatic acridinium ester, an imidazole, an acridinium salt and oxalate esters), bioluminescent compounds (e.g., luciferin, luciferase and aequorin), paramagnetic labels (e.g., chromium (III), manganese (III), manganese (III), iron (II), iron (III), cobalt (II), nickel (II), copper (II), praseodymium (III), neodymium (III), samarium (III), gadolinium (III), terbium (III), dysprosium (III), holmium (III), erbium (III) and ytterbium (III)) which can be detected by MRI, and adhesion proteins (e.g., biotin, streptavidin, avidin, and other lectins).

Additional candidate functions include cytotoxicity (e.g., bacterial cholera toxin, pertussis toxin, anthrax toxin lethal factor, Pseudomonas exotoxin A, diphtheria toxin, plant toxin ricin, radionuclides such as $^{47}$Sc $^{67}$Cu, $^{72}$Se, $^{88}$Y, $^{90}$Sr, $^{90}$Y, $^{97}$Ru, $^{99}$Tc, $^{105}$Rh, $^{111}$In, $^{125}$I, $^{131}$I, $^{149}$Tb, $^{153}$Sm, $^{186}$Re, $^{188}$Re, $^{194}$Os, $^{203}$Pb, $^{211}$At, $^{212}$Bi, $^{213}$Bi, $^{212}$Pb, $^{223}$Ra, $^{225}$Ac, $^{227}$Ac, $^{228}$Th, and cytotoxic drugs). Modified antibodies therefore also include addition of functional entities, covalently or non-covalently attached to the antibodies of the invention.

Multifunctional antibodies can be produced through chemical crosslinking of the selected molecules (which have been produced by synthetic means or by expression of nucleic acid that encode the polypeptides), via an amino acid linker sequence or through recombinant DNA technology combined with in vitro, or cellular expression of the polypeptide. Multispecific antibodies can be similarly produced through recombinant technology and expression, fusion of hybridomas (e.g., to produce quadromas) that produce antibodies with different epitopic specificities, or expression of multiple nucleic acid encoding antibody variable chains with different epitopic specificities in a single cell. The coupling of such agents can be performed using conventional methods known in the art (see, for example, R. Reisfeld and S. Sell Eds. Monoclonal Antibodies and Cancer Therapy, Alan R. Liss Inc. NY, 1985; and U.S. Pat. Nos. 5,558,852 and 5,624,659)

Polypeptide sequences can be made using recombinant DNA technology of polypeptide encoding nucleic acids via cell expression or in vitro translation, or chemical synthesis of polypeptide chains using methods known in the art. Antibodies of the invention, including modified forms and subsequences can be expressed from recombinantly produced antibody-encoding nucleic acid (see, e.g., Harlow and Lane, Using Antibodies: A Laboratory Manual, Cold Spring Harbor Laboratory, 1999; Fitzgerald et al., J.A.C.S. 117:11075 (1995); Gram et al, Proc. Natl. Acad. Sci. USA 89:3576 (1992)). Antibodies may also be produced by expressing encoding nucleic acids in mammalian, insect, and plant cells. Polypeptide sequences including antibodies can also be produced by a chemical synthesizer (see, e.g., Applied Biosystems, Foster City, Calif.).

The invention further provides nucleic acids encoding invention antibodies, including modified forms thereof. In various embodiments, a nucleic acid encodes a sequence of a heavy or light chain amino acid sequence set forth of RM4. In a particular aspect, a nucleic acid encodes a sequence of a heavy or light chain amino acid sequence of RM4.

As used herein, a "nucleic acid," refers to at least two or more ribo- or deoxy-ribonucleic acid base pairs (nucleotides) that are linked through a phosphoester bond or equivalent. Nucleic acids include polynucleotides and polynucleosides. Nucleic acids include single, double or triplex, circular or linear, molecules. A nucleic acid molecule may belong exclusively or in a mixture to any group of nucleotide-containing molecules, as exemplified by, but not limited to: RNA, DNA, cDNA, genomic nucleic acid, non-genomic nucleic acid, naturally occurring and non naturally occurring nucleic acid and synthetic nucleic acid.

Nucleic acids can be of any length. Nucleic acid lengths typically range from about 20 nucleotides to 10 Kb, 10 nucleotides to 5 Kb, 1 to 5 Kb or less, 1000 to about 500 nucleotides or less in length. Nucleic acids can also be shorter, for example, 100 to about 500 nucleotides, or from about 12 to 25, 25 to 50, 50 to 100, 100 to 250, or about 250 to 500 nucleotides in length.

Nucleic acids further include modifications such as nucleotide and nucleoside substitutions, additions and deletions, as well as derivatized forms and fusion sequences (e.g., encoding recombinant polypeptide). For example, due to the degeneracy of the genetic code, nucleic acids include sequences and subsequences degenerate with respect to nucleic acids that encode amino acid sequences of RM4. Other examples are nucleic acids complementary to a sequence that encodes an amino acid sequence of RM4. Nucleic acid deletions (subsequences) have from about 10 to 25, 25 to 50 or 50 to 100 nucleotides. Such nucleic acids are useful for expressing polypeptide fragments, for genetic manipulation (as primers and templates for PCR amplification), and as probes to detect the presence or an amount of a sequence encoding an invention antibody in vitro, in a cell, culture medium, biological sample (e.g., tissue, organ, blood or serum), or in a subject.

In yet another example of nucleic acid modifications, nucleic acids that hybridize at high stringency to nucleic acids that encode an amino acid sequence of RM4, a subsequence thereof and nucleic acid sequences complementary to the encoding nucleic acids, are provided. Hybridizing nucleic acids are useful for detecting the presence or an amount of a sequence encoding an invention antibody in vitro, or in a cell, culture medium, biological sample (e.g., tissue, organ, blood or serum), or in a subject.

The term "hybridize" refers to the binding between nucleic acid sequences. Hybridizing sequences will generally have more than about 50% homology to a nucleic acid that encodes an amino acid sequence of RM4. The hybridization region between hybridizing sequences can extend over at least about 10-15 nucleotides, 15-20 nucleotides, 20-30 nucleotides, 30-50 nucleotides, 50-100 nucleotides, or about 100 to 200 nucleotides or more.

As is understood by those skilled in the art, the $T_M$ (melting temperature) is the temperature at which binding between two nucleic acid sequences is no longer stable. For two sequences to bind, the temperature of a hybridization reaction must be less than the calculated $T_M$ for the sequences under the hybridization conditions. The $T_M$ is influenced by the amount of sequence complementarity, length, composition (% GC), type of nucleic acid (RNA vs. DNA), and the amount of salt, detergent and other components in the reaction (e.g., formamide). All of these factors are considered in establishing appropriate hybridization conditions (see, e.g., the hybridization techniques and formula for calculating $T_M$ described in Sambrook et al, In: Molecular Cloning: A Laboratory Manual, 3rd ed., Cold Spring Harbor Laboratory Press, 2001).

Typically, wash conditions are adjusted to attain the desired degree of hybridization stringency. Thus, hybridization stringency can be determined empirically, for example, by washing under particular conditions, e.g., at low stringency conditions or high stringency conditions. Optimal conditions for selective hybridization will vary depending on the particular hybridization reaction involved. An example of high stringency hybridization conditions are as follows: 2×SSC/0.1% SDS at about 37.degree. C. or 42.degree. C. (hybridization conditions); 0.5×SSC/0.1% SDS at about room temperature (low stringency wash); 0.5×SSC/0.1% SDS at about 42.degree. C. (moderate stringency wash); and 0.1×SSC/0.1% SDS at about 65.degree. C. (high stringency wash).

Nucleic acids can be produced using various standard cloning and chemical synthesis techniques. Such techniques include, but are not limited to nucleic acid amplification, e.g., polymerase chain reaction (PCR), with genomic DNA or cDNA targets using primers (e.g., a degenerate primer mixture) capable of annealing to antibody encoding sequence; and chemical synthesis of nucleic acid sequences. The sequences produced can then be translated in vitro, or cloned into a plasmid and propagated and then expressed in a cell (e.g., microorganism, such as yeast or bacteria, a eukaryote such as an animal or mammalian cell or in a plant).

The invention further provides expression cassettes including a nucleic acid encoding an invention antibody operably linked to an expression control element. As used herein, the term "operably linked" refers to a physical or a functional relationship between the elements referred to that permit them to operate in their intended fashion. Thus, an expression control element "operably linked" to a nucleic acid means that the control element modulates nucleic acid transcription and as appropriate, translation of the transcript.

Physical linkage is not required for the elements to be operably linked. For example, a minimal element can be linked to a nucleic acid encoding an invention antibody. A second element that controls expression of an operably linked nucleic acid encoding a protein that functions "in trans" to bind to the minimal element can influence expression of the antibody. Because the second element regulates expression of antibody, the second element is operably linked to the nucleic acid encoding the antibody even though it is not physically linked.

The term "expression control element" refers to nucleic acid that influences expression of an operably linked nucleic acid. Promoters and enhancers are particular non-limiting examples of expression control elements. A "promotor sequence" is a DNA regulatory region capable of initiating transcription of a downstream (3' direction) coding sequence. The promoter sequence includes a number of nucleotides necessary to facilitate transcription initiation. Enhancers also regulate gene expression, but can function a distance from the transcription start site of the gene to which it is operably linked. Enhancers function at either 5' or 3' ends of the gene, as well as within the gene (e.g., in introns or coding sequences). Additional expression control elements include leader sequences and fusion partner sequences, internal ribosome binding sites (IRES) elements for the creation of multigene, or polycistronic, messages, splicing signal for introns, maintenance of the correct reading frame of the gene to permit in-frame translation of mRNA, polyadenylation signal to provide proper polyadenylation of the transcript of a gene of interest, and stop codons.

Expression control elements include "constitutive" elements such that transcription of the operably linked nucleic acid occurs without the presence of a signal or stimuli. Expression control elements that confer expression in response to a signal or stimuli, which either increases or decreases expression of the operably linked nucleic acid, are "regulatable." A regulatable element that increases expression of the operably linked nucleic acid in response to a signal or stimuli is referred to as an "inducible element." A regulatable element that decreases expression of the operably linked nucleic acid in response to a signal or stimuli is referred to as a "repressible element" (i.e., the signal decreases expression; when the signal is removed or absent, expression is increased).

Expression control elements include elements active in a particular tissue or cell type, referred to as "tissue-specific expression control elements." Tissue-specific expression control elements are typically active in specific cell or tissue types because they are recognized by transcriptional activator proteins, or other regulators of transcription, that are unique to the specific cell or tissue type.

Expression control elements include full-length nucleic acid sequences, such as native promoter and enhancer elements, as well as subsequences or nucleotide variants thereof (e.g., substituted/mutated or other forms that differ from native sequences) which retain all or part of full-length or non-variant control element function (confer regulation, e.g., retain some amount of inducibility in response to a signal or stimuli).

For bacterial expression, constitutive promoters include T7, as well as inducible promoters such as pL of bacteriophage λ, plac, ptrp, ptac (ptrp-lac hybrid promoter). In insect cell systems, constitutive or inducible promoters (e.g., ecdysone) may be used. In yeast, constitutive promoters include, for example, ADH or LEU2 and inducible promoters such as GAL (see, e.g., Ausubel et al., In: Current Protocols in Molecular Biology, Vol. 2, Ch. 13, ed., Greene Publish. Assoc. & Wiley Interscience, 1988; Grant et al., (1987) In: Methods in Enzymology, 153:516-544, eds. Wu & Grossman, 1987, Acad. Press, N.Y.; Glover, DNA Cloning, Vol. II, Ch. 3, IRL Press, Wash., D.C., 1986; Bitter (1987) In: Methods in Enzymology, 152:673-684, eds. Berger & Kimmel, Acad. Press, N.Y.; and, Strathem et al, The Molecular Biology of the Yeast Saccharomyces (1982) eds. Cold Spring Harbor Press, Vols. I and II).

For mammalian expression, constitutive promoters of viral or other origins may be used. For example, SV40, or viral long terminal repeats (LTRs) and the like, or inducible promoters derived from the genome of mammalian cells (e.g., metallothionein IIA promoter; heat shock promoter, steroid/thyroid hormone/retinoic acid response elements) or from mammalian viruses (e.g., the adenovirus late promoter; the inducible mouse mammary tumor virus LTR) are used.

The invention also provides stably and transiently transformed cells and progeny thereof into which a nucleic acid molecule encoding an invention antibody has been introduced by means of recombinant DNA techniques in vitro, ex vivo or in vivo. The transformed cells can be propagated and the introduced nucleic acid transcribed, or encoded protein expressed. Transformed cells include but are not limited to prokaryotic and eukaryotic cells such as bacteria, fungi, plant, insect, and animal (e.g., mammalian, including human) cells. In one particular aspect, the cell is a hybridoma. The cells may be present in culture, in a cell, tissue or organ ex vivo or a subject. A progeny cell may not be identical to the parental cell, since there may be mutations that occur during replication.

The term "transformed" means a genetic change in a cell following incorporation of nucleic acid (e.g., a transgene) exogenous to the cell. Thus, a "transformed cell" is a cell into which, or a progeny of which a nucleic acid molecule has been introduced by means of recombinant DNA techniques. Cell transformation to produce host cells may be carried out as described herein or using techniques known in the art. Accordingly, methods of producing cells including the nucleic acids and cells expressing the invention antibodies are also provided.

Typically, cell transformation employs a "vector," which refers to a plasmid, virus, such as a viral vector, or other vehicle known in the art that can be manipulated by insertion or incorporation of a nucleic acid. For genetic manipulation "cloning vectors" can be employed, and to transcribe or translate the inserted polynucleotide "expression vectors" can be employed. Such vectors are useful for introducing nucleic acids, including a nucleic acid that encodes an antibody operably linked with an expression control element, and expressing the antibody in vitro (e.g., in solution or in solid phase), in cells or in a subject in vivo.

A vector generally contains an origin of replication for propagation in a cell. Control elements, including expression control elements as set forth herein, present within a vector, can be included to facilitate transcription and translation.

Vectors can include a selection marker. A "selection marker" is a gene that allows for the selection of cells containing the gene. "Positive selection" refers to a process whereby only cells that contain the selection marker will survive upon exposure to the positive selection. Drug resistance is one example of a positive selection marker; cells containing the marker will survive in culture medium containing the selection drug, and cells lacking the marker will die. Selection markers include drug resistance genes such as neo, which confers resistance to G418; hygr, which confers resistance to hygromycin; and puro which confers resistance to puromycin. Other positive selection marker genes include genes that allow identification or screening of cells containing the marker. These genes include genes for fluorescent proteins (GFP and GFP-like chromophores, luciferase), the lacZ gene, the alkaline phosphatase gene, and surface markers such as CD8, among others. "Negative selection" refers to a process whereby cells containing a negative selection marker are killed upon exposure to an appropriate negative selection agent. For example, cells which contain the herpes simplex virus-thymidine kinase (HSV-tk) gene (Wigler et al., Cell 11:223 (1977)) are sensitive to the drug gancyclovir (GANC). Similarly, the gpt gene renders cells sensitive to 6-thioxanthine.

Viral vectors included are those based on retroviral, adeno-associated virus (AAV), adenovirus, reovirus, lentivirus, rotavirus genomes, simian virus 40 (SV40) or bovine papilloma virus (Cone et at, Proc. Natl. Acad. Sci. USA 81:6349 (1984); Eukaryotic Viral Vectors, Cold Spring Harbor Laboratory, Gluzman ed., 1982; Sarver et al., Mol. Cell. Biol. 1:486 (1981)). Additional viral vectors useful for expression include parvovirus, rotavirus, Norwalk virus, coronaviruses, paramyxo and rhabdoviruses, togavirus (e.g., sindbis virus and semliki forest virus) and vesicular stomatitis virus (VSV).

Mammalian expression vectors include those designed for in vivo and ex vivo expression, such as AAV (U.S. Pat. No. 5,604,090). AAV vectors have previously been shown to provide expression of Factor IX in humans and in mice at levels sufficient for therapeutic benefit (Kay et al., Nat. Genet. 24:257 (2000); Nakai et al., Blood 91:4600 (1998)). Adenoviral vectors (U.S. Pat. Nos. 5,700,470, 5,731,172 and 5,928,944), herpes simplex virus vectors (U.S. Pat. No. 5,501,979) retroviral (e.g., lentivirus vectors are useful for infecting dividing as well as non-dividing cells and foamy viruses) vectors (U.S. Pat. Nos. 5,624,820, 5,693,508, 5,665, 577, 6,013,516 and 5,674,703 and WIPO publications WO92/05266 and WO92/14829) and papilloma virus vectors (e.g., human and bovine papilloma virus) have all been employed in gene therapy (U.S. Pat. No. 5,719,054). Vectors also include cytomegalovirus (CMV) based vectors (U.S. Pat. No. 5,561,063). Vectors that efficiently deliver genes to cells of the intestinal tract have been developed (see, e.g., U.S. Pat. Nos. 5,821,235, 5,786,340 and 6,110,456).

Introduction of antibodies and nucleic acid encoding invention antibodies into target cells can also be carried out by methods known in the art such as osmotic shock (e.g., calcium phosphate), electroporation, microinjection, cell fusion, etc. Introduction of nucleic acid and polypeptide in vitro, ex vivo and in vivo can also be accomplished using other techniques. For example, a polymeric substance, such as polyesters, polyamine acids, hydrogel, polyvinyl pyrrolidone, ethylenevinylacetate, methylcellulose, carboxymethylcellulose, protamine sulfate, or lactide/glycolide copolymers, polylactide/glycolide copolymers, or ethylenevinylacetate copolymers. A nucleic acid can be entrapped in microcapsules prepared by coacervation techniques or by interfacial polymerization, for example, by the use of hydroxymethylcellulose or gelatin-microcapsules, or poly(methylmethacrolate) microcapsules, respectively, or in a colloid drug delivery system. Colloidal dispersion systems include macromolecule complexes, nano-capsules, microspheres, beads, and lipid-based systems, including oil-in-water emulsions, micelles, mixed micelles, and liposomes.

Liposomes for introducing various compositions into cells, including nucleic acids, including, for example, phosphatidylcholine, phosphatidylserine, lipofectin and DOTAP, are known to those skilled in the art (see, e.g., U.S. Pat. Nos. 4,844,904, 5,000,959, 4,863,740, 4,975,282, GIBCO-BRL, Gaithersburg, Md.). piperazine based amphilic cationic lipids useful for gene therapy also are known (see, e.g., U.S. Pat. No. 5,861,397). Cationic lipid systems also are known (see, e.g., U.S. Pat. No. 5,459,127). Accordingly, viral and non-viral vector means of delivery into cells or tissue, in vitro, in vivo and ex vivo are included.

The invention therefore also provides methods of producing antibodies of the invention. In one embodiment, a method includes: introducing a nucleic acid that encodes the antibody into a host cell or a translation extract; incubating said host cell or extract under conditions whereby said nucleic acid is expressed as a translation product including said antibody; and isolating or purifying the antibody. In one aspect, the nucleic acid encodes RM4. In another aspect, the nucleic acid encodes modified RM4 (e.g., a variant or subsequence).

The invention antibodies also can be combined with any other compounds or agents that may provide an enhanced or synergistic therapeutic benefit. The invention therefore also provides combination compositions including an invention antibody and one or more additional compounds or agents and methods of using the combinations. For example, an invention antibody may be combined with a compound or agent that has anti-tumor activity or immune enhancing activity. In a particular example, RM4 is combined with RM2.

As used here, the term "immune enhancing," when used in reference to a compound, agent, therapy or treatment, means that the compound agent, therapy or treatment, provides an increase, stimulation, induction or promotion of an immune response, humoral or cell-mediated. Such therapies can enhance immune response generally, or enhance immune response to a specific target tumor.

Specific non-limiting examples of immune enhancing agents include monoclonal, polyclonal antibody and mixtures thereof. Antibodies include antibodies that bind to tumor-associated antigens (TAA). The term "tumor associated antigen" or "TAA" refers to an antigen expressed by a tumor cell. TAAs may be expressed in amounts greater in tumor cells than a normal non-tumor cell counterpart, or may be expressed at similar levels, or at levels less than a normal cell counterpart.

Particular non-limiting examples of TAAs that can be targeted and TAA binding antibodies include, for example, human IBD12 monoclonal antibody which binds to epithelial cell surface H antigen (U.S. Pat. No. 4,814,275); M195 antibody which binds to leukemia cell CD33 antigen (U.S. Pat. No. 6,599,505); monoclonal antibody DS6 which binds to ovarian carcinoma CA6 tumor-associated antigen (U.S. Pat. No. 6,596,503); and BR96 antibody which binds to Lex carbohydrate epitope expressed by colon, breast, ovary, and lung carcinomas. Additional anti-tumor antibodies that can be employed include, for example, Rituxan®, Herceptin (anti-Her-2 neu antibody), Bevacizumab (Avastin), Zevalin, Bexxar, Oncolym, 17-1A(Edrecolomab), 3F8 (anti-neuroblastoma antibody), MDX-CTLA4, Campath®, Mylotarg and IMC-C225 (Cetuximab).

Antibody RM2 is produced by a human IgG secreting cell line derived using standard somatic cell hybridization technology (ATCC deposit No. PTA-5411; Example 1). RM2 binds to a peptide sequence termed AgRM2 of approximately 52 kDa, as determined by denaturing gel electrophoresis. AgRM2 is expressed at least in part on the cell surface. AgRM2 is more highly expressed in proliferating cells than in non-proliferating cells, e.g., hyperproliferating cells. AgRM2 is present on metastatic or non-metastatic lung, skin (melanoma), pancreatic, and brain (neuroblastoma/glioma) cancer cells.

Other non-limiting examples of TAAs that can be targeted with an antibody include MUC-1, HER-2/neu, MAGE, p53, T/Tn and CEA (Breast cancer); MUC-2 and MUC-4, CEA, p53 and the MAGE (colon cancer); MAGE, MART-1 and gp100 (melanoma); GM2, Tn, sTn, Thompson-Friedenreich antigen (TF), MUC 1, MUC2, beta chain of chorionic gonadotropin (hCG beta), HER2/neu, PSMA and PSA (prostate cancer); chorionic gonadotropin (testicular cancer); and alpha fetoprotein (hepato-cellular carcinoma).

Additional examples of immune enhancing agents include immune cells such as lymphocytes, plasma cells, macrophages, NK cells and B-cells expressing antibody against the tumor. Cytokines that enhance or stimulate immunogenicity against tumor such as IL-2, IL-1α, IL-1β, IL-3, IL-6, IL-7, granulocyte-macrophage-colony stimulating factor (GMCSF), IFN-γ, IL-12, TNF-α, and TNFβ are also non-limiting examples of immune enhancing agents. Chemokines including MIP-1α, MIP-1β, RANTES, SDF-1, MCP-1, MCP-2, MCP-3, MCP-4, eotaxin, eotaxin-2, 1-309/TCA3, ATAC, HCC-1, HCC-2, HCC-3, LARC/MIP-3α, PARC, TARC, CKβ, CKβ6, CKβ7, CKβ8, CKβ9, CKβ11, CKβ12, C10, IL-8, GROα, GROβ, ENA-78, GCP-2, PBP/CTAβIIIβ-TG/NAP-2, Mig, PBSF/SDF-1, and lymphotactin are additional non-limiting examples of immune enhancing agents.

As used herein, an "anti-tumor," "anti-cancer" or "anti-neoplastic" treatment, therapy, activity or effect means any compound, agent, therapy or treatment regimen or protocol that inhibits, decreases, slows, reduces or prevents hyperplastic, tumor, cancer or neoplastic growth, metastasis, proliferation or survival. Anti-tumor compounds, agents, therapies or treatments can operate by disrupting, inhibiting or delaying cell cycle progression or cell proliferation; stimulating or enhancing apoptosis, lysis or cell death, inhibiting nucleic acid or protein synthesis or metabolism, inhibiting cell division, or decreasing, reducing or inhibiting cell survival, or production or utilization of a necessary cell survival factor, growth factor or signaling pathway (extracellular or intracellular). Examples of anti-tumor therapy include chemotherapy, immunotherapy, radiotherapy (ionizing or chemical), local thermal (hyperthermia) therapy and surgical resection.

Specific non-limiting examples of chemical agent classes having anti-cell proliferative and anti-tumor activities include alkylating agents, anti-metabolites, plant extracts, plant alkaloids, nitrosoureas, hormones, nucleoside and nucleotide analogues. Specific examples of drugs include cyclophosphamide, azathioprine, cyclosporin A, prednisolone, melphalan, chlorambucil, mechlorethamine, busulphan, methotrexate, 6-mercaptopurine, thioguanine, 5-fluorouracil, cytosine arabinoside, AZT, 5-azacytidine (5-AZC) and 5-azacytidine related compounds, bleomycin, actinomycin D, mitycin, mitomycin C, carmustine, lomustine, semustine, streptozotocin, hydroxyurea, cisplatin, mitotane, procarbazine, dacarbazine, taxot, vinblastine, vincristine, doxorubicin and dibromomannitol.

The invention further provides kits including one or more antibodies of the invention, including pharmaceutical formulations, packaged into suitable packaging material. In one embodiment, a kit includes an antibody or modified form of RM4. In another embodiment, a kit includes a nucleic acid encoding an antibody or modified form of RM4. In additional embodiments, a kit includes nucleic acids that further include an expression control element; an expression vector; a viral expression vector; an adeno-associated virus expression vector; an adenoviral expression vector; and a retroviral expression vector. In yet an additional embodiment, a kit includes a cell that expresses an invention antibody or modified form, e.g., RM4. In still further embodiments, a kit includes a compound or agent having anti-tumor or immune-enhancing activity, for example, an alkylating agent, anti-metabolite, plant alkaloid, plant extract, antibiotic, nitrosourea, hormone, nucleoside analogue, nucleotide analogue, antibody that binds a TAA.

As used herein, the term "packaging material" refers to a physical structure housing the components of the kit. The packaging material can maintain the components sterilely, and can be made of material commonly used for such purposes (e.g., paper, corrugated fiber, glass, plastic, foil, ampules, etc.). The label or packaging insert can include appropriate written instructions, for example, practicing a method of the invention, e.g., detecting a hyperproliferative disorder, treating a hyperprolferative disorder, etc. Kits of the invention therefore can additionally include instructions for using the kit components in a method.

Thus, in additional embodiments, a kit includes a label or packaging insert including instructions for expressing an invention antibody or a nucleic acid encoding an invention antibody in cells in vitro, in vivo, or ex vivo. In yet additional embodiments, a kit includes a label or packaging insert including instructions for treating a subject (e.g., a subject having or at risk of having a cell proliferative disorder such as a tumor) with an invention antibody or a nucleic acid encoding an invention antibody in vivo, or ex vivo. In further embodiments, a kit includes a label or packaging insert including instructions for detecting the presence or expression level of AgRM4 in vitro or in vivo.

Instructions can therefore include instructions for practicing any of the methods of the invention described herein. For example, invention pharmaceutical compositions can be included in a container, pack, or dispenser together with instructions for administration to a subject. Instructions may additionally include indications of a satisfactory clinical endpoint or any adverse symptoms that may occur, or additional information required by regulatory agencies such as the Food and Drug Administration for use on a human subject.

The instructions may be on "printed matter," e.g., on paper or cardboard within the kit, on a label affixed to the kit or packaging material, or attached to a vial or tube containing a component of the kit. Instructions may comprise voice or video tape and additionally be included on a computer readable medium, such as a disk (floppy diskette or hard disk), optical CD such as CD- or DVD-ROM/RAM, magnetic tape, electrical storage media such as RAM and ROM and hybrids of these such as magnetic/optical storage media.

Invention kits can additionally include a buffering agent, a preservative, or a protein/nucleic acid stabilizing agent. The kit can also include control components for assaying for activity, e.g., a control sample or a standard. Each component of the kit can be enclosed within an individual container or in a mixture and all of the various containers can be within single or multiple packages.

Antibodies, including modified forms, can be used for detection and diagnostic purposes. The invention therefore also provides methods of detecting AgRM4. In one embodiment, a method includes: contacting AgRM4, or a sample that may contain AgRM4 with an antibody that binds to AgRM4 under conditions allowing binding; and determining the presence of AgRM4. Detecting AgRM4 indicates the presence of AgRM4. In one aspect, the detecting is in vitro. In another aspect, the detecting is in vivo. Thus, in another embodiment, a method of detecting the presence of AgRM4 in a subject includes: contacting a subject or a sample from a subject with an antibody that binds to AgRM4 under conditions allowing the antibody to bind to AgRM4; and assaying for the presence of AgRM4 in the subject or in the sample. The presence of AgRM4 indicates the presence of AgRM4 in the subject, Because antibodies of the invention can be used to detect AgRM4, the invention further provides methods for detecting expression levels of AgRM4.

Methods of identifying compounds that inhibit or stimulate expression of AgRM4 are provided. In one embodiment, a method includes: contacting a cell that expresses or is capable of expressing AgRM4 with a test compound; and detecting expression of AgRM4. A change in expression in the presence of the test compound indicates that the test compound inhibits or stimulates AgRM4 expression.

The antibodies of the invention, including subsequences, modified forms, encoding nucleic acids, etc., can be incorporated into pharmaceutical compositions. Such pharmaceutical compositions are useful for administration to a subject in vivo or ex vivo, and for providing therapy for a physiological disorder or condition treatable with an invention antibody, e.g., a hyperproliferative disorder (tumor) of the brain, lung, skin, pancreas, breast, colon or gut.

Pharmaceutical compositions include "pharmaceutically acceptable" and "physiologically acceptable" carriers, diluents or excipients. As used herein the terms "pharmaceutically acceptable" and "physiologically acceptable" include solvents (aqueous or non-aqueous), solutions, emulsions, dispersion media, coatings, isotonic and absorption promoting or delaying agents, compatible with pharmaceutical administration. Such formulations can be contained in a liquid; emulsion, suspension, syrup or elixir, or solid form; tablet (coated or uncoated), capsule (hard or soft), powder, granule, crystal, or microbead. Supplementary compounds (e.g., preservatives, antibacterial, antiviral and antifungal agents) can also be incorporated into the compositions.

Pharmaceutical compositions can be formulated to be compatible with a particular local or systemic route of administration. Thus, pharmaceutical compositions include carriers, diluents, or excipients suitable for administration by particular routes. Specific non-limiting examples of routes of administration for compositions of the invention are parenteral, e.g., intravenous, intradermal, intramuscular, subcutaneous, oral, transdermal (topical), transmucosal, and rectal administration.

Solutions or suspensions used for parenteral, intradermal, or subcutaneous application can include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Pharmaceutical compositions for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyetheylene glycol, and the like), and suitable mixtures thereof. Fluidity can be maintained, for example, by the use of a coating such as lecithin, by the maintenance of the required particle size in the case of dispersion and by the use of surfactants. Antibacterial and antifungal agents include, for example, parabens, chlorobutanol, phenol, ascorbic acid and thimerosal. Isotonic agents, for example, sugars, polyalcohols such as mannitol, sorbitol, sodium chloride can be included in the composition. Including an agent which delays absorption, for example, aluminum monostearate and gelatin can prolong absorption of injectable compositions.

Sterile injectable solutions can be prepared by incorporating the active compound in the required amount in an appropriate solvent with one or a combination of above ingredients followed by filtered sterilization. Generally, dispersions are prepared by incorporating the active compound into a sterile vehicle containing a basic dispersion medium and other ingredients as above. In the case of sterile powders for the preparation of sterile injectable solutions, methods of preparation include, for example, vacuum drying and freeze-drying which yields a powder of the active ingredient plus any additional desired ingredient from a previously sterile-filtered solution thereof.

For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays, inhalation devices (e.g., aspirators) or suppositories. For transdermal administration, the active compounds are formulated into ointments, salves, gels, creams or patches.

Invention antibodies, including s modified forms and nucleic acids encoding them, can be prepared with carriers that protect against rapid elimination from the body, such as a controlled release formulation or a time delay material such as glyceryl monostearate or glyceryl stearate. The compositions can also be delivered using implants and microencapsulated delivery systems to achieve local or systemic sustained delivery or controlled release.

Biodegradable, biocompatible polymers can be used, such as ethylene vinyl acetate, polyanhydrides, polyglycolic acid, collagen, polyorthoesters, and polylactic acid. Methods for preparation of such formulations are known to those skilled in the art. The materials can also be obtained commercially from Alza Corporation and Nova Pharmaceuticals, Inc. Liposomal suspensions (including liposomes targeted to cells or tissues using antibodies or viral coat proteins) can also be used as pharmaceutically acceptable carriers. These can be prepared according to methods known to those skilled in the art, for example, as described in U.S. Pat. No. 4,522,811.

Additional pharmaceutical formulations appropriate for administration are known in the art (see, e.g., Gennaro (ed.), Remington: The Science and Practice of Pharmacy, 20th ed., Lippincott, Williams & Wilkins (2000); Ansel et al., Pharmaceutical Dosage Forms and Drug Delivery Systems, 7th ed., Lippincott Williams & Wilkins Publishers (1999); Kibbe (ed.), Handbook of Pharmaceutical Excipients American Pharmaceutical Association, 3rd ed. (2000); and Pharmaceutical Principles of Solid Dosage Forms, Technonic Publishing Co., Inc., Lancaster, Pa., (1993)).

The pharmaceutical formulations can be packaged in dosage unit form for ease of administration and uniformity of dosage. "Dosage unit form" as used herein refers to physically discrete units suited as unitary dosages treatment; each unit contains a predetermined quantity of active compound in association with the pharmaceutical carrier or excipient calculated to produce the desired therapeutic effect.

Thus, the invention provides methods for inhibiting or preventing proliferation of a cell that expresses AgRM4. In one embodiment, a method includes contacting a cell that expresses AgRM4 with an amount of antibody that binds to AgRM4 sufficient to inhibit or prevent proliferation of the cell. In one aspect, the cell is a proliferating cell, e.g., a hyperproliferating cell. In another aspect, the hyperproliferating cell is a metastatic or non-metastatic cancer cell. In particular aspects, the cell is selected from a brain, lung, skin, pancreas, breast colon or gut cell.

The cell may be present in a subject, for example, a mammal (e.g., human subject) having or at risk of having a hyperproliferative disorder. Thus, the invention also provides methods of treating a hyperproliferative cell disorder in a subject wherein at least a portion of the hyperproliferative cells express AgRM4. In one embodiment, the antibody is administered to a subject in an amount sufficient to treat the hyperproliferative cell disorder. In one aspect, the hyperproliferative disorder comprises a tumor.

Further provided are methods of treating a subject having or at risk of having a tumor. In one embodiment, a method includes administering to the subject an amount of human monoclonal antibody designated RM4 that selectively binds to an antigen designated AgRM4, sufficient to treat the subject. In additional embodiments, a method includes administering to the subject an amount of antibody having the binding specificity of human monoclonal antibody designated RM4; administering to the subject an amount of antibody that competes for the binding of human monoclonal antibody designated RM4 to AgRM4; and administering to the subject an amount of antibody that binds to an epitope of AgRM4 to which human monoclonal antibody designated RM4 binds, sufficient to treat the subject. In one aspect, a method also includes administering an immune enhancing or anti-tumor agent, such as an anti-tumor antibody (e.g., RM2).

As used herein, the term "hyperproliferate," and grammatical variations thereof, when used in reference to a cell, tissue or organ, refers to undesirable, excessive or abnormal cell, tissue or organ proliferation, differentiation or survival. Proliferative and differentiative disorder include diseases and physiological conditions, both benign and neoplastic, characterized by undesirable, excessive or abnormal cell numbers, cell growth or cell survival in a subject. Specific examples of such disorders include metastatic and non-metastatic tumors and cancers.

The terms "tumor," "cancer," "malignancy," and "neoplasia" are used interchangeably herein and refer to a cell or population of cells of any cell or tissue origin, whose growth, proliferation or survival is greater than growth, proliferation or survival of a normal counterpart cell, e.g. a cell proliferative or differentiative disorder. Such disorders include, for example, carcinoma, sarcoma, melanoma, neural, and reticuloendothelial or haematopoietic neoplastic disorders (e.g., myeloma, lymphoma or leukemia). Tumors can arise from a multitude of primary tumor types, including but not limited to breast, lung, thyroid, head and neck, brain, lymphoid, gastrointestinal (mouth, esophagus, stomach, small intestine, colon, rectum), genito-urinary tract (uterus, ovary, cervix, bladder, testicle, penis, prostate), kidney, pancreas, liver, bone, muscle, skin, and may metastasize to secondary sites. Tumors can be in any stage, e.g., a stage I, II, III, IV or V tumor, or in remission.

A "solid tumor" refers to neoplasia or metastasis that typically aggregates together and forms a mass. Specific examples include visceral tumors such as melanomas, breast, pancreatic, uterine and ovarian cancers, testicular cancer, including seminomas, gastric or colon cancer, hepatomas, adrenal, renal and bladder carcinomas, lung, head and neck cancers and brain tumors/cancers.

Carcinomas refer to malignancies of epithelial or endocrine tissue, and include respiratory system carcinomas, gastrointestinal system carcinomas, genitourinary system carcinomas, testicular carcinomas, breast carcinomas, prostatic carcinomas, endocrine system carcinomas, and melanomas. The term also includes carcinosarcomas, e.g., which include malignant tumors composed of carcinomatous and sarcomatous tissues. Adenocarcinoma includes a carcinoma of a glandular tissue, or in which the tumor forms a gland like structure. Melanoma refers to malignant tumors of melanocytes and other cells derived from pigment cell origin that may arise in the skin, the eye (including retina), or other regions of the body, including the cells derived from the neural crest that also gives rise to the melanocyte lineage. Additional carcinomas can form from the uterine/cervix, lung, head/neck, colon, pancreas, testes, adrenal gland, kidney, esophagus, stomach, liver and ovary.

Sarcomas refer to malignant tumors of mesenchymal cell origin. Exemplary sarcomas include for example, lymphosarcoma, liposarcoma, osteosarcoma, chondrosarcoma, leiomyosarcoma, rhabdomyosarcoma and fibrosarcoma.

Neural neoplasias include glioma, glioblastoma, meningioma, neuroblastoma, retinoblastoma, astrocytoma, oligodendrocytoma A "liquid tumor" refers to neoplasia of the reticuloendothelial or haematopoetic system, such as a lymphoma, myeloma, or leukemia, or a neoplasia that is diffuse in nature. Particular examples of leukemias include acute and chronic lymphoblastic, myeolblastic and multiple myeloma. Typically, such diseases arise from poorly differentiated acute leukemias, e.g., erythroblastic leukemia and acute megakaryoblastic leukemia. Specific myeloid disorders include, but are not limited to, acute promyeloid leukemia (APML), acute myelogenous leukemia (AML) and chronic myelogenous leukemia (CML); lymphoid malignancies include, but are not limited to, acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinernia (WM). Specific malignant lymphomas include, non-Hodgkin lymphoma and variants, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Methods of the invention include providing a detectable or measurable improvement in the subjects condition: a therapeutic benefit. A therapeutic benefit is any objective or subjective transient or temporary, or longer term improvement in the condition or a reduction in the severity or adverse symptom of the condition. Thus, a satisfactory clinical endpoint is achieved when there is an incremental or a partial reduction in the severity or duration or frequency of one or more associated adverse symptoms or complications, or inhibition or reversal of one or more of the physiological, biochemical or cellular manifestations or characteristics of the condition. A therapeutic benefit or improvement ("ameliorate" is used synonymously) therefore need not be complete destruction of all target hyperproliferating cells (e.g., tumor) or ablation of all adverse symptoms or complications associated with the disorder. For example, inhibiting an increase in tumor cell mass (stabilization of a disease) can reduce mortality and prolong lifespan even if only for a few days, weeks or months, and even though some or most of the tumor remains.

Specific non-limiting examples of therapeutic benefit include a reduction in tumor volume (size or cell mass), inhibiting an increase in tumor volume, slowing or inhibiting tumor progression or metastasis, stimulating tumor cell lysis or apoptosis. Examination of a biopsied sample containing a tumor (e.g., blood or tissue sample), can establish whether a reduction in numbers of tumor cells or inhibition of tumor cell proliferation has occurred. Alternatively, for a solid tumor, invasive and non-invasive imaging methods can ascertain a reduction in tumor size, or inhibiting increases in tumor size.

Adverse symptoms and complications associated with tumor, neoplasia, and cancer that can be reduced or decreased include, for example, nausea, lack of appetite, lethargy, pain and discomfort. Thus, a reduction in the severity, duration or frequency of adverse symptoms, an improvement in the subjects subjective feeling, such as increased energy, appetite, psychological well being, are examples of therapeutic benefit.

The doses or "sufficient amount" for treatment to achieve a therapeutic benefit or improvement are effective to ameliorate one, several or all adverse symptoms or complications of the condition, to a measurable or detectable extent, although preventing or inhibiting a progression or worsening of the disorder, condition or adverse symptom, is a satisfactory outcome. Thus, in the case of a hyperproliferative condition or disorder, the amount of antibody will be sufficient to provide a therapeutic benefit to the subject or to ameliorate the condition or symptom. The dose may be proportionally increased or reduced as indicated by the status of the disease being treated or the side effects of the treatment.

Doses also considered effective are those that result in reduction of the use of another therapeutic regimen or protocol. For example, an antibody of the invention is considered as having a therapeutic benefit if its administration results in less chemotherapeutic drug, radiation or immunotherapy being required for tumor treatment.

Of course, as is typical for treatment protocols, some subjects will exhibit greater or less response to treatment. For example, appropriate amounts will depend upon the condition treated (e.g., the tumor type or stage of the tumor), the therapeutic effect desired, as well as the individual subject (e.g., the bioavailability within the subject, gender, age, etc.).

The invention antibodies also can be administered in association with any other therapeutic regimen or treatment protocol. Other treatment protocols include drug treatment (chemotherapy), surgical ressection, hyperthermia, radiotherapy, and immunotherapy, as set forth herein and known in the art. The invention therefore provides methods in which the antibodies of the invention are used in combination with any anti-cell proliferative therapeutic regimen or treatment protocol, such as those set forth herein or known in the art.

Radiotherapy includes internal or external delivery to a subject. For example, alpha, beta, gamma and X-rays can administered to the subject externally without the subject internalizing or otherwise physically contacting the radioisotope. Specific examples of X-ray dosages administered range from daily doses of 50 to 200 roentgens for prolonged periods of time (3 to 5/week), to single doses of 2000 to 6000 roentgens. Dosages vary widely, and depend on duration of exposure, the half-life of the isotope, the type of radiation emitted, the cell type and location treated and the progressive stage of the disease.

The term "subject" refers to animals, typically mammalian animals, such as a non-human primate (gorillas, chimpanzees, orangutans, macaques, gibbons), a domestic animal (dogs and cats), a farm animal (horses, cows, goats, sheep, pigs), experimental animal (mouse, rat, rabbit, guinea pig) and humans. Subjects include disease model animals (e.g., such as mice and non-human primates) for testing in vivo efficacy of antibodies of the invention (e.g., a tumor animal model). Human subjects include adults, and children, for example, newborns and older children, between the ages of 1 and 5, 5 and 10 and 10 and 18.

Subjects include humans having or at risk of having a hyperproliferative disorder, such as subjects having a cell or tissue that expresses AgRM4, or subjects that have a family history of, are genetically predisposed to, or have been previously afflicted with a hyperproliferative disorder. Thus, subjects at risk for developing cancer can be identified with genetic screens for tumor associated genes, gene deletions or gene mutations. Subjects at risk for developing breast cancer lack Breal, for example. Subjects at risk for developing colon cancer have deleted or mutated tumor suppressor genes, such as adenomatous polyposis coli (APC), for example.

Unless otherwise defined, all technical and scientific terms used herein have the same meaning as commonly understood by one of ordinary skill in the art to which this invention relates. Although methods and materials similar or equivalent to those described herein can be used in the practice or testing of the invention, suitable methods and materials are described herein.

All publications, patents and other references cited herein are incorporated by reference in their entirety. In case of conflict, the present specification, including definitions, will control.

As used herein, singular forms "a", "and," and "the" include plural referents unless the context clearly indicates otherwise. Thus, for example, reference to "an antibody" includes a plurality of such antibodies and reference to "a sequence" can include reference to all or a part of or one or more sequences, and so forth.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

This example describes characteristics of human monoclonal antibody RM2 (ATCC deposit No. PTA-5411).

Generation of RM2:

Pooled regional draining lymph nodes from patients with colon and pancreatic cancers were obtained from surgical specimens at biopsy, processed under sterile conditions and then stimulated in vitro with pokeweed mitogen (PWM; Borrebaeck, C. (ed) in vitro Immunization in Hybridoma Technology; Elsevier Publisher, New York, 1988). Briefly, nodal segments were immersed in serum-free RPMI 1640 media, trimmed free of extraneous tissue and capsular components, and teased with nugent forceps to make a single cell suspension. Cells remaining in suspension after larger aggregates settled were removed and washed twice (500×g for 5 min). All dissections and cell preparations were performed at room temperature. The isolated lymphocytes were resuspended at $5 \times 10^6$/ml in RPMI 1640 medium supplemented with 10% FCS and PWM (Borrebaeck, C. (ed), supra) and subsequently incubated overnight at 37 c in 5% CO2/95% air prior to fusion.

Using 35% Polyethylede Glycol 1500, $3.3 \times 10^7$ patient's lymphocytes were fused with $1.6 \times 10^7$ TMr-RN15 cells using standard hybridoma generation protocols (Harlow and Lane, supra). After the fusion, the cells were added to 96-well microtiter plates at $1 \times 10^5$ cells/well. The day after the fusion the growth medium was replaced by RPMI 1640 medium supplemented with 10% FCS and 2 mM glutamine, including hypoxanthine ($1 \times 10^{-4}$M), amethopterin ($4 \times 10^{-7}$M), and thymidine (1.6×10^-5 M) [HAT media]. After 2 to 4 weeks in culture, hybrids visible to the eye were further analyzed for human antibody production. Those found to secrete antibody were expanded and cloned by limiting dilution without any feeder layer cells in standard RPMI 1640 medium supplemented with 10% FCS.

TABLE 1

RM2 EIA Cell Line Reactivity Profile

| Cell Line | Reactivity |
|---|---|
| Brain | |
| U-87 MG | + |
| MC-IXC | + |
| Lung | |
| SK-LU-1 | + |
| A549 | + |
| Calu-1 | + |
| NCI-H661 | + |
| Melanoma | |
| A375 | + |
| Me Wo | + |
| SK-MEL-28 | + |
| Pancreatic | |
| PANC-1 | + |
| Capan-1 | + |
| Breast | |
| SK-BR-3 | − |
| MCF-7 | − |
| Colon | |
| Colo205 | − |
| HT-29 | − |
| LoVo | − |
| Caco-2 | − |
| SK-CO-1 | − |
| Hematopoietic | |
| Daudi | − |
| Raji | − |
| Ovary | |
| Caov-4 | − |
| SK-OV-3 | − |
| Skin | |
| A431 | − |

Immunohistochemistry:

Tissue tin sections (5 u thick) from fresh surgical biopsy specimens were prepared by cryostat and mounted on glass slides for evaluation (Harlow and Lane, supra). RM2 was added first to the slides, incubated for 45 min, washed, and incubated another 45 min with a biotinylated secondary goat anti-human IgG, followed by avidin-horseradish peroxidase. The sections were counter stained with Evan's blue/hematoxylin and mounted. These results are shown in Table 2.

TABLE 2

| | RM2 |
|---|---|
| Tumor Tissue | |
| Breast | 1/1 |
| Colon | 0/6 (0/2) |
| Lung | 7/7 (2/2) |
| Melanoma | 9/9 (3/3) |
| Pancreatic | 4/4 |
| Leukemia | 0/4 |

TABLE 2-continued

| | RM2 |
|---|---|
| Lymphoma | 0/4 |
| Normal Tissue | |
| Adrenal gland | 0/3 |
| Breast | 0/4 |
| Bronchus | 0/3 |
| Esophagus | 0/3 |
| Gallbladder | 0/3 |
| Heart | 0/3 |
| Intestine | 0/5 |
| Kidney | 0/4 |
| Liver | 0/3 |
| Lung | 0/3 |
| Muscle | 0/3 |
| Ovary | 0/3 |
| Pancreas | 0/3 |
| Prostate | 0/3 |
| Skin | 0/3 |
| Spleen | 0/3 |
| Stomach | 0/3 |
| Testis | 0/3 |
| Thyroid | 0/3 |
| Tongue | 0/3 |
| Tonsil | 0/3 |
| Urinary Bladder | 0/3 |

RM2 Purification:

Antibody containing supernatants from the RM2 clone were pooled, concentrated, and purified with Protein G chromatography. The column was extensively washed to remove non-bound proteins. RM2 antibody was eluted from the column using low pH and subsequently analyzed for activity.

Biodistribution:

Purified RM2 was labeled with 125-I using a standard chloramine-T procedure. 1.0 mg of RM2 was combined with 125-I (14-17 mCi/ug) at an iodine:protein ratio of 1:10 in 12×75 tubes. Ten ul of chloramine-T per 100 ug protein were added and incubated for 3 min at room temperature. The reaction was stopped with 10 ul of sodium metabisulfite per 100 ug protein. Nonbound 125-I was removed by using a G-50-80 centrifuge column. Specific activities were between 0.2-1.0 mCi/mg (0.02-0.1 mCi/100 ug RM2). 4×10^6 PANC-1 cells were implanted subcutaneously on the left flanks of 5 female athymic mice (nu/nu; 4-6 weeks old). When tumor volumes were about 200-300 mm^3 each mouse was given 100 ul of 125-I labeled RM2 via tail vein. 48 hours later the mice were sacrificed and the tumor, blood, and major organs were removed, weighed, and counted in a gamma scintillation counter. These results are shown in Table 3.

TABLE 3

| Organs | RM2 (PANC1) |
|---|---|
| tumor | 30.4 |
| liver | 11.9 |
| spleen | 11.5 |
| kidney | 2.4 |
| lung | 3.4 |
| muscle | 3.8 |
| heart | 2.5 |
| stomach | 4.9 |
| intestine | 3.1 |
| bone | 2.7 |
| blood | 8.9 |

Tumor Regression:

On day zero, fifteen female athymic mice (nu/nu; 4-6 weeks old) were each injected with 4×10^6 PANC-1 cells in the left flank and divided into three groups of five mice each. On day 7, Group 1 received 100 ul injections of PBS, Group 2 received 100 ul injections of 100 ug of control (irrelevant) IgG, and Group 3 received 100 ul injections of 100 ug of RM2. On day 10, each Group received a second injection of their respective treatments. On day 14 each Group received a third injection and on day 21 each Group received their last injection. Each mouse was evaluated and tumor measured on the same day, once a week. This data is shown in FIG. 1.

Tumor Volume at each week following injection expressed numerically is summarized in Table 7.

Example 2

This example describes the isolation of Human Monoclonal Antibody RM4, the tissue and antigen binding characteristics of the antibody and the sequence of the antibody.

Generation of RM4:

Pooled regional draining lymph nodes from patients with colon cancer were obtained from surgical specimens at biopsy and processed under sterile conditions. Briefly, the nodal segments were immersed in serum-free RPMI 1640 media, trimmed free of extraneous tissue and capsular components, and teased with nugent forceps to make a single cell suspension. Cells remaining in suspension after larger aggregates settled were removed and washed twice (500×g for 5 min). All dissections and cell preparations were performed at room temperature. The isolated lymphocytes were resuspended at $5\times10^6$/ml in RPMI 1640 medium supplemented with 10% FCS and incubated overnight at 37 c in 5% CO2/95% air prior to fusion.

Using 35% Polyethylede Glycol 1500, $3.3\times10^7$ patient's lymphocytes were fused with $1.6\times10^7$ RN15 cells using standard hybridoma generation protocols (Harlow and Lane, supra). After the fusion, the cells were added to 96-well microtiter plates at $1\times10^5$ cells/well. The day after the fusion the growth medium was replaced by RPMI 1640 medium supplemented with 10% FCS and 2 mM glutamine, including hypoxanthine ($1\times10^{-4}$M), amethopterin ($4\times10^{-7}$M), and thymidine ($1.6\times10^{-5}$M) [HAT media]. After 2 to 4 weeks in culture, hybrids visible to the eye were further analyzed for human antibody production. Those found to secrete antibody were expanded and cloned by limiting dilution without any feeder layer cells in standard RPMI 1640 medium supplemented with 10% FCS.

Antibody Assay:

Quantitation of human immunoglobulin was assessed by standard enzyme immunoassays (EIA) as previously described (Harlow and Lane, supra).

RM4 Specificity:

To assess the specificity of RM4 the antibody was screened against a panel of human cell lines and this data is shown in Table 4. The cell lines were obtained from the American Type Culture Collection (ATCC) and immobilized on assay plates for analysis. Briefly, logarithmic phase cells were collected, washed in PBS, resuspended, aliquoted at $2\times10^5$ cells per well in flat-bottomed Immulon 96-well plates, and placed overnight in a 37 c drying oven (Harlow, E. and Lane, D. Antibodies. A Laboratory Manual; Cold Spring Harbor Laboratory, New York, 1988). To these cells, RM4 antibody supernatant was added, incubated, washed, and developed with horseradish peroxidase-conjugated goat anti-human IgG. All tests were done in triplicate and read on a micro-plate EIA reader.

TABLE 4

RM4 RM4 EIA Cell Line Reactivity Profile

| Cell Line | Reactivity |
|---|---|
| Breast | |
| MDA-MB-361 | + |
| SK-BR-3 | + |
| MCF-7 | + |
| Colon | |
| WiDr | + |
| Colo205 | + |
| LoVo | + |
| LST174 | + |
| HT-29 | + |
| Gastric | |
| KATO-III | + |
| Lung | |
| SK-LU-1 | + |
| NCI-H661 | + |
| NCI-H1435 | + |
| Calu-1 | + |
| A549 | + |
| Brain | |
| U-87 MG | − |
| MC-ICX | − |
| Hematopoietic | |
| Raji | − |
| Daudi | − |
| EB1 | − |
| Melanoma | |
| A375 | − |
| Me Wo | − |
| SK-MEL-28 | − |
| Ovary | |
| Caov-4 | − |
| SK-OV-3 | − |
| Pancreatic | |
| Capan-1 | − |
| PANC-1 | − |
| Skin | |
| A431 | − |

Immunohistochemistry:

Tissue thin sections (5 u thick) from fresh surgical biopsy specimens were prepared by cryostat and mounted on glass slides for evaluation (Harlow and Lane, supra). RM4 was added first to the slides, incubated for 45 min, washed, and incubated another 45 min with a biotinylated secondary goat anti-human IgG, followed by avidin-horseradish peroxidase. The sections were counter stained with Evan's blue/hematoxylin and mounted. These results are shown in Table 5.

TABLE 5

| Tumor Tissue | RM4 |
|---|---|
| Breast | 4/4 |
| Colon | 8/8 (2/2) |
| Lung | 7/7 (3/3) |
| Melanoma | 0/4 (0/2) |
| Pancreatic | 0/3 |
| Leukemia | 0/4 |
| Lymphoma | 0/4 |
| Normal Tissue | 0/3 |
| Adrenal gland | 0/3 |

TABLE 5-continued

| Tumor Tissue | RM4 |
|---|---|
| Breast | 0/3 |
| Bronchus | 0/3 |
| Esophagus | 0/3 |
| Gallbladder | 0/3 |
| Heart | 0/4 |
| Intestine | 0/3 |
| Kidney | 0/3 |
| Liver | 0/3 |
| Lung | 0/3 |
| Muscle | 0/3 |
| Ovary | 0/3 |
| Pancreas | 0/3 |
| Prostate | 0/3 |
| Skin | 0/4 |
| Spleen | 0/3 |
| Stomach | 0/3 |
| Testis | 0/3 |
| Thyroid | 0/3 |
| Tongue | 0/3 |
| Tonsil | 0/3 |
| Urinary Bladder | 0/3 |

RM4 Purification:

Antibody supernatants from the RM4 clone were pooled, concentrated, and purified with Protein C chromatography. The column was extensively washed to remove non-bound proteins. RM4 antibody was eluted from the column using low pH and subsequently analyzed for activity.

Biodistribution:

Purified RM4 was labeled with 125-I using a standard chloramine-T procedure. 1.0 mg of RM4 was combined with 125-I (14-17 mCi/ug) at an iodine:protein ratio of 1:10 in 12×75 tubes. Ten ul of chloramine-T per 100 ug protein were added and incubated for 3 min at room temperature. The reaction was stopped with 10 ul of sodium metabisulfite per 100 ug protein. Nonbound 125-I was removed by using a G-50-80 centrifuge column. Specific activities were between 0.2-1.0 mCi/mg (0.02-0.1 mCi/100 ug RM3). $4 \times 10^6$ SK-BR-3 cells were implanted subcutaneously on the left flanks of 5 female athymic mice (nu/nu; 4-6 weeks old). When tumor volumes were about 200-300 mm$^3$ each mouse was given 100 ul of 125-I labeled RM4 via tail vein. 48 hours later the mice were sacrificed and the tumor, blood, and major organs were removed, weighed, and counted in a gamma scintillation counter. These results are shown in Table 6.

TABLE 6

| Organs | RM4 (SK-BR-3) |
|---|---|
| tumor | 8.9 |
| liver | 7.2 |
| spleen | 7.4 |
| kidney | 1.3 |
| lung | 3.4 |
| muscle | 1.4 |
| heart | 1.1 |
| stomach | 1.4 |
| intestine | 2.3 |
| bone | 1.2 |
| blood | 4.2 |

Figure 2:
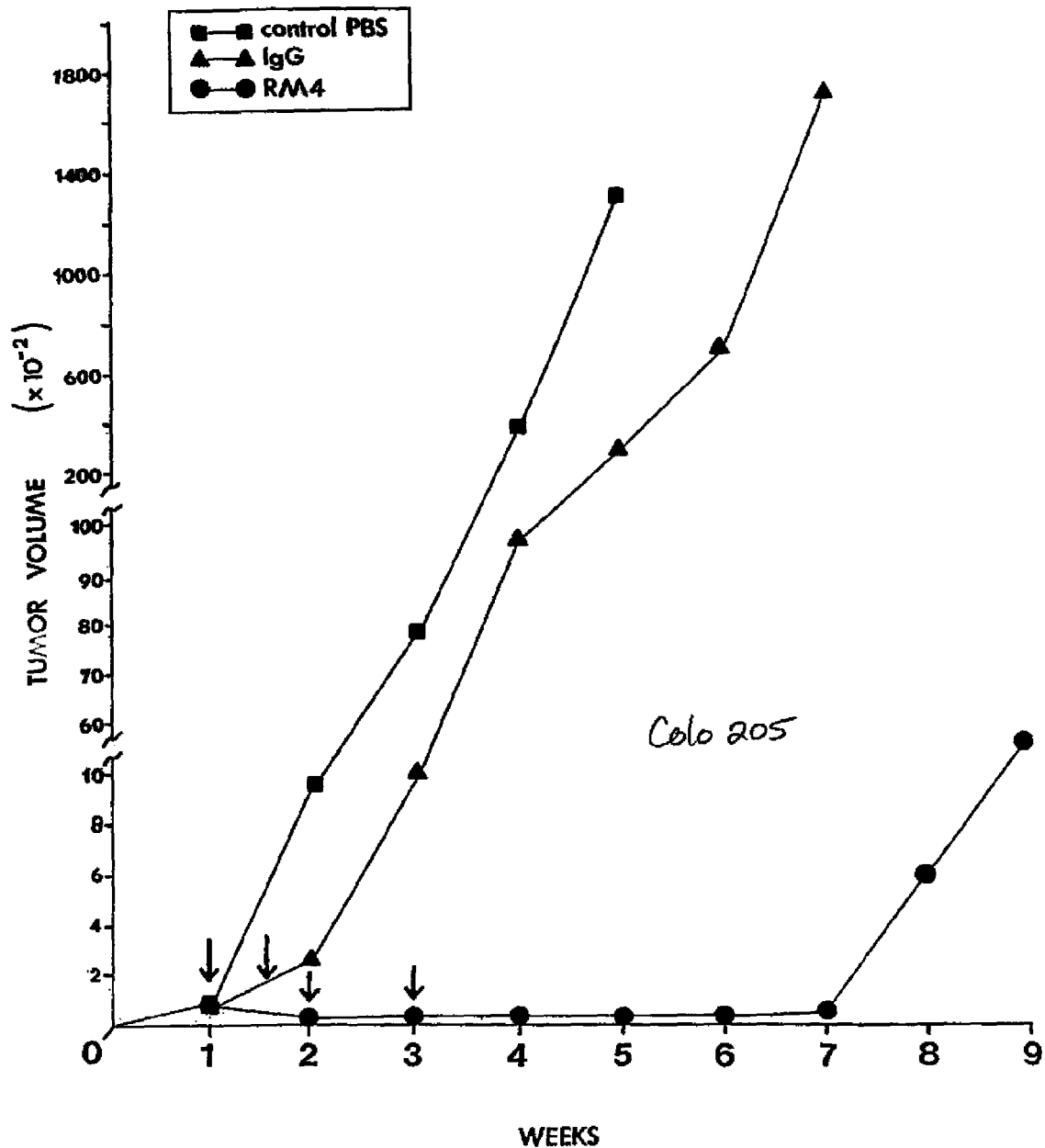
FIG. 2 shows tumor (Colo205 cells, a colon cancer cell line) necrosis in mice following injection with RM4. Tumor volume for each week following injection is illustrated.

Tumor Regression:

On day zero, fifteen female athymic mice (nu/nu; 4-6 weeks old) were each injected with $4 \times 10^{16}$ Colo205 cells in the left flank and divided into three groups of five mice each. On day 7, Group 1 received 100 ul injections of PBS, Group 2 received 100 ul injections of 100 ug of control (irrelevant) IgG, and Group 3 received 100 ul injections of 100 ug of RM4. On day 10, each Group received a second injection of their respective treatments. On day 14 each Group received a third injection and on day 21 each Group received their last injection. Each mouse was evaluated and tumor measured on the same day, once a week. This data is shown in FIG. 2. Tumor Volume at each week following injection expressed numerically is summarized in Table 7.

Antigen Analysis:

No antigen was detected using standard western blot procedures. This suggests that either AgRM4 is not a protein, is a conformation dependent structure, or is bound to the non-protein fraction of cells.

FACS analysis has shown AgRM4 to cell proliferation dependent. Cells in stationary phase growth do not express cell surface AgRM4. Cells growing logarithmically express AgRM4 at high levels.

TABLE 7

| | Week 1 | Week 2 | Week 3 | Week 4 | Week 5 | Week 6 | Week 7 | Week 8 | Week 9 |
|---|---|---|---|---|---|---|---|---|---|
| | | | | | Colo205 | | | | |
| Control | 128 ± 46 | 1132 ± 581 | 8289 ± 212 | 47323 ± 18969 | 130483 ± 18640 | | | | |
| Human IgG | 120 ± 52 | 308 ± 90 | 1760 ± 395 | 9850 ± 2861 | 32979 ± 3041 | 82009 ± 19519 | 170749 ± 31873 | | |
| RM4 | 128 ± 46 | 77 ± 121 | 9 ± 6 | 16 ± 4 | 16 ± 5 | 26 ± 12 | 60 ± 62 | 613 ± 534 | 2288 ± 948 |
| | | | | | Panc-1 | | | | |
| Control | 45 ± 16 | 1677 ± 379 | 10435 ± 3728 | 64244 ± 12008 | 12229 ± 40601 | | | | |
| Human IgG | 36 ± 22 | 592 ± 712 | 12312 ± 2963 | 42968 ± 9477 | 97656 ± 25317 | 161964 ± 35267 | | | |
| RM2 | 36 ± 22 | 9 ± 6 | 5 ± 3 | 10 ± 5 | 10 ± 5 | 10 ± 5 | 8 ± 0 | 10 ± 6 | 10 ± 5 |

Example 3

This example describes the synergistic activity of RM4 in combination with antibody RM2.

Figure 3:
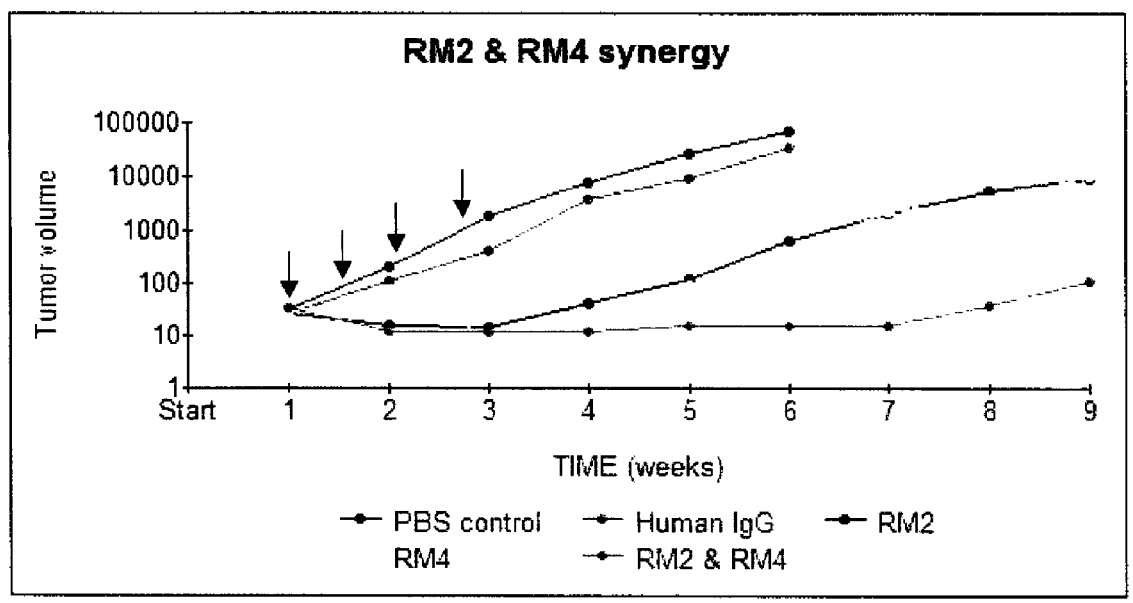
FIG. 3 shows tumor (Calu-1 cells, a lung cancer cell line) necrosis in mice following injection with RM2 and RM4. Arrows indicate injections on days 7, 10, 14 and 18.

In brief, fifteen female athymic mice (nu/nu; 4-6 weeks old) were each injected with 4×10^6 Calu 1 cells (lung tumor) at day 0 as described above. On day 7, Group 1 received 100 ul injections of PBS, Group 2 received 100 ul injections of 100 ug of control (irrelevant) IgG, and Group 3 received 100 ul injections of 100 ug of RM4. On day 10, each Group received a second injection of their respective treatments. On day 14 each Group received a third injection and on day 21 each Group received their last injection. Each mouse was evaluated and tumor measured on the same day, once a week. This data is shown in FIG. 3.

What is claimed is:

1. An isolated human monoclonal antibody designated RM4 having the amino acid sequence of the antibody produced by the hybridoma having the ATCC deposit number 5412 and that selectively binds to an antigen designated AgRM4, or an antigen binding fragment thereof.

2. The antibody of claim 1, wherein the antibody comprises an Fab, Fab', Fv, F(ab')$_2$, Fd, or a single chain Fv.

3. The antibody of claim 1, where the antibody contains a cytotoxic molecule.

4. The antibody of claim 3, wherein the cytotoxic molecule is selected from a bacterial toxin, plant toxin, radionuclide, cytotoxic drug, or cytokine.

5. The antibody of claim 4, wherein the radionuclide is an alpha, beta or gamma emitter.

6. The antibody of claim 1, wherein the antibody contains a detectable label or tag.

7. The antibody of claim 6, wherein the detectable label is selected from a radioisotope, fluorescent compound, colloidal metal, chemiluminescent compound, bioluminescent compound, enzyme or a paramagnetic label.

8. An isolated human monoclonal antibody designated RM4 having the amino acid sequence of the antibody produced by the hybridoma having the ATCC deposit number 5412 and that selectively binds to an antigen designated AgRM4 or an antigen binding fragment thereof, wherein the antigen designated AgRM4 is expressed on the surface of hyperproliferating cells including MDA-MB-361, SK-BR-3, MCF-7, WiDr, Colo205, LoVo, LST174, HT-29, KATO-III, SK-LU-1, NCI-H661, NCI-H1435, Calu-1, A549.

9. The antibody of claim 1, wherein the antigen designated AgRM4 is expressed at least in part on the cell surface.

10. A composition comprising the antibody of claim 1, and one or more anti-tumor or immune enhancing agents.

11. A kit comprising the composition of claim 8.

12. A kit comprising the antibody of claim 1.

13. The antibody of claim 8, wherein the AgRM4 antigen is not detectable by the RM4 antibody in cell lines including MC-ICX, Raji, Daudi, EB1, A375, Me Wo, SK-MEL-28, Caov-4, SK-OV-3, Capan-1, PANC-1, and A431.

14. The antibody of claim 8, wherein the antibody is modified and comprises an Fab, Fab', Fv, F(ab')$_2$, Fd, or a single chain Fv.

15. The antibody of claim 8, wherein the antibody contains a cytotoxic molecule.

16. The antibody of claim 15, wherein the cytotoxic molecule is selected from a bacterial toxin, plant toxin, radionuclide, cytotoxic drug, or cytokine.

17. The antibody of claim 16, wherein the radionuclide is an alpha, beta or gamma emitter.

18. The antibody of claim 8, wherein the antibody contains a detectable label or tag.

19. The antibody of claim 18, wherein the detectable label is selected from a radioisotope, fluorescent compound, colloidal metal, chemiluminescent compound, bioluminescent compound, enzyme or a paramagnetic label.

* * * * *